(12) United States Patent
Trnovsky et al.

(10) Patent No.: US 6,586,176 B1
(45) Date of Patent: Jul. 1, 2003

(54) GEL MICRODROPS IN GENETIC ANALYSIS

(75) Inventors: Jan Trnovsky, Saugus, MA (US); Patricia McGrath, Cambridge, MA (US)

(73) Assignee: Cellay, LLC, Cambridge, MA (US)

( * ) Notice: Subject to any disclaimer, the term of this patent is extended or adjusted under 35 U.S.C. 154(b) by 0 days.

(21) Appl. No.: 09/369,640

(22) Filed: Aug. 6, 1999

Related U.S. Application Data

(60) Provisional application No. 60/095,721, filed on Aug. 7, 1998.

(51) Int. Cl.[7] .............................. C12Q 1/68; C12N 5/02; C07H 21/04; C07H 1/00
(52) U.S. Cl. .......................... 435/6; 435/325; 536/23.1; 536/24.3; 536/123.1
(58) Field of Search .......................... 435/6, 91.2, 126, 435/325, 7.1; 536/123.1, 24.33, 24.3, 23.1, 120

(56) References Cited

U.S. PATENT DOCUMENTS

| | | | |
|---|---|---|---|
| 4,973,683 A | * 11/1990 | Lindgren | 536/120 |
| 5,451,500 A | 9/1995 | Stapleton | 435/6 |
| 5,552,270 A | 9/1996 | Khrapko et al. | 435/6 |
| 5,665,582 A | 9/1997 | Kausch et al. | |
| 5,784,162 A | 7/1998 | Cabib et al. | |
| 5,861,247 A | 1/1999 | Mizabekov et al. | 435/6 |

FOREIGN PATENT DOCUMENTS

EP          0 626 455 A1     11/1994

OTHER PUBLICATIONS

Nguyen et al. In Situ Hybridization to chromosomes stabilized in gel microdrops. Cytometry vol. 21, pp. 111–119, Oct. 1995.*

Ahern. Biochemical, Reagent Kits offer scientists good return on investment. The Scientist vol. 9, No. 15, pp. 1–5, Jul. 1995.*

Weaver et al. Gel Microdrop technology for rapid isolation of rare and high producer cells. Nature Medicine vol. 3, No. 5, pp. 583–585, May 1997.*

Jackson et al. A cell–cycle–dependent DNA polymerase Activity that replicates intact DNA in chromatin. J. Mol. Biol. vol. 192, pp. 65–76, Nov. 1986.*

Nguyen et al., "In Situ Hybridization to Chromosomes Stabilized in Gel Microdrops" Cytometry, vol. 21, pp. 111–119 (1995).*

Trnovsky et al., "Indentification of chromosomal translocations in agarose–encapsulated chromosomes by FISH", Cytomery, pp753.*

Trnovsky et al., "Flow cytometric sorting of chromosomes encapsulated in agarose gel microdrops after in situ hybridization", pp. 46.*

Arnold et al., "Indentification of complex chromosome rearrangements in the gibbon by fluorescent in situ hybridization (FISH) of a human chromosome 2q specific microlibrary, yeast artificial chromosomes, and reciprocal chromosome painting," *Cytogenetics and Cell Genetics*, 74:80–85 (1996).

Matthews et al., "Analytical Strategies for the Use of DNA Probes," *Analytical Biochemistry*, 169:1–25 (1988).

Ryan et al., "Rapid Assay for Mycobacterial Growth and Antibiotic Susceptibility Using Gel Microdrop Encapsulation," *J. Clinical Microbiology*, 33(7):1720–1726 (1995).

Thompson et al., "Cytogenetic Profiling Using Fluorescence In Situ Hybridization (FISH) and Comparative Genomic Hybridization (CGH)," *J. Cellular Biochemistry*, 17G:139–143 (1993).

Trnovsky et al., "Flow cytometric sorting of chromosomes encapsulated in agarosc gel microdrops after in situ hybridization," *Clinical Chemistry*, 42(11):46 (1996).

Trnovsky et al., "Identification of chromosomal translocations in agarose–encapsulated chromosomes by FISH and flow cytometry," *American J. of Human Genetics*, 59(4):A135 (1996).

Weaver et al., "Rapid Clonal Growth Measurements at the Single–Cell Level: Gel Microdroplets and Flow Cytometry," *Biotechnology*, 9(9):873–877 (1991).

Nguyen et al., "In Situ Hybridization to Chromosomes Stabilized in Gel Microdrops," *Cytometry*, 21:111–119 (95).

Matthews et al., "Analytical Strategies for the Use of DNA Probes," *Analytical Biochem.*, 169:1–25 (1988).

Stratagene, "Gene Characterization Kits," 1988 Stratagene Catalog, p. 39, (1988).

* cited by examiner

*Primary Examiner*—Kenneth R. Horlick
*Assistant Examiner*—Cynthia Wilder
(74) *Attorney, Agent, or Firm*—Townsend and Townsend and Crew LLP

(57) ABSTRACT

The invention provides methods of nucleic acid analysis. Such methods entail forming a population of gel microdrops encapsulating a population of biological entities, each entity comprising a nucleic acid, whereby at least some microdrops in the population each encapsulate a single entity. The population of gel microdrops is then contacted with a probe under conditions whereby the probe specifically hybridizes to at least one complementary sequence in the nucleic acid in at least one gel microdrop. At least one gel microdrop is then analyzed or detected. The biological entities can be cells, viruses, nuclei and chromosomes.

22 Claims, 8 Drawing Sheets

FIG. 3
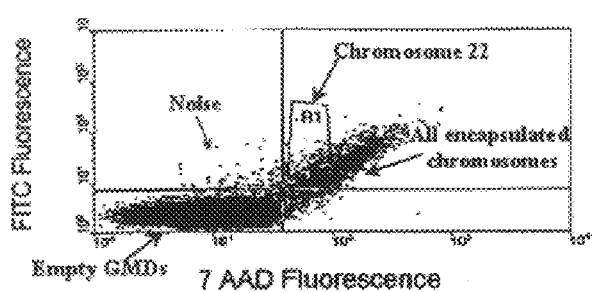 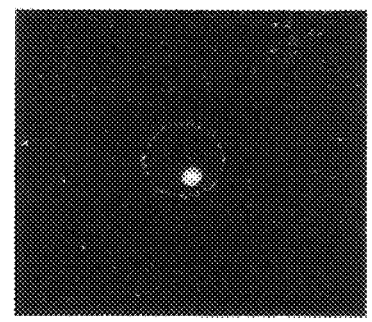

GEL MICRODROPS IN GENETIC ANALYSIS

CROSS-REFERENCE TO RELATED APPLICATION

The present application derives priority from U.S. Ser. No. 60/095,721, filed Aug. 7, 1998, which is incorporated by reference in its entirety for all purposes.

STATEMENT OF GOVERNMENT RIGHTS

The work described in this application may have supported in part by grants 2R44CA68969-02 and 2R44CA78141-02 from the Department of Health and Human Services of the U.S. Government. The U.S. Government may have certain rights in this invention.

TECHNICAL FIELD

The present invention resides in the field of genetic analysis.

BACKGROUND

Cytogenetic testing is still in its infancy. Current cytogenetic methods are limited to analysis of gene aberrations easily detectable in cells, nuclei, or chromosomes, in part, because slide based methods are highly manual. Analysis of aberrations present in low frequency is not routinely performed in the clinical setting because many slides of cells, nuclei or chromosomes would have to be evaluated to establish statistical frequency.

Banding is the classical approach used for analyzing chromosomes in metaphase spreads. This method is based on staining which results in dark bands in the region of the chromosome where the chromatin occurs at higher density. The banding pattern is specific for each chromosome and allows identification for karyotyping, which is the determination of each chromosome's copy number. However, banding resolution is not sufficient to detect small deletions or additions of chromosomal mass, which occur in a variety of disease conditions, particularly in cancers.

Fluorescent in situ hybridization is another approach used to localize genomic DNA fragments or to paint whole chromosomes and to detect and characterize genetic abnormalities including translocations (31, 40), aneusomy (41, 42), and gene amplification (43). These genetic abnormalities can be detected in individual cells, chromosomes, or nuclei to assess of tumor genotype, analyze genetic heterogeneity, and detect malignant cells. To preserve integrity in FISH applications, chromosomes are typically adsorbed onto glass slides for analysis. Analysis therefore requires microscopic evaluation of individual slides limiting automation and rapid sample processing. Fluorescent in situ hybridizations prepared on glass slides rely not only on the assay and reagents but on the instrumentation and the expertise and ingenuity of the scientists using it resulting in poor reproducibility. An inherent limitation to this technology is that at least 100 kb of DNA sequence in a single cell must be present for detection (68–70). In addition, harsh conditions for fixing either tissue or intact cells to a glass slide are less than optimal: up to 90% of the assay sample can be lost from the glass support.

Some chromosomes can also be resolved by fluorescent staining followed by flow cytometry (14,15). Successful chromosome sorting is, however, dependent on the binding characteristics of fluorescent dyes and the extent to which the chromosome of interest can be distinguished from chromosomes of similar size, clumps of chromosomes, and debris containing DNA (13). Although this approach has resulted in the construction of yeast artificial chromosome (YAC) libraries for mapping studies (16) in species which have chromosomes of similar size, such as mouse, arabidopsis, and 20% of the human chromosomes, unambiguous resolution has not been possible. Flow sorting based on dye uptake is possible for well resolved chromosomes, but this method works poorly for chromosomes which are similar in size and base composition, mainly human chromosomes 9–12 and the majority of mouse chromosomes. Furthermore, flow cytometry cannot currently be used to analyze hybridized chromosomes prepared by conventional methods because unfixed chromosomes fall apart using high temperatures and/or formamide.

SUMMARY OF THE CLAIMED INVENTION

The invention provides methods of nucleic acid analysis. Such methods entail forming a population of gel microdrops encapsulating a population of biological entities, each entity comprising a nucleic acid, whereby at least some microdrops in the population each encapsulate a single entity. Nucleic acids can be DNA or RNA. The population of gel microdrops is then contacted with a probe under conditions whereby the probe specifically hybridizes to at least one complementary sequence in the nucleic acid in at least one gel microdrop. At least one gel microdrop is then analyzed or detected. The biological entities can be cells, viruses, nuclei and chromosomes.

In some methods, at least 10,000 biological entities are encapsulated. In some methods, the biological entities are not fixed chemically before the contacting step. In some methods, nucleic acids are amplified before the contacting step. Suitable materials for forming droplets include agarose, alginate, carrageenan, or polyacrylamide.

In some methods, nucleic acids are recovered from microdrops by digestion with agarase. Optionally, the recovered DNA can be digested with a restriction enzyme with or without prior digestion of agarase. In some methods, the gel matrix is crosslinked with itself and/or nucleic acid being analyzed, typically, between the denaturation and contacting steps. In some method, the hybridization is performed at a temperature of over 68° C. or in the presence of a formamide concentration greater than 20%. In some methods, the microdrops further comprise a reagent that amplifies a signal from the labelled probe. For example, the probe can be labelled with an enzyme, and the reagent can be a substrate for the enzyme.

In some methods, microdrops are isolated by FACS™. In some methods, the biological entities are a population of chromosomes obtained from a population of different cells in a patient. In some methods, the ratio of a subpopulation of microdrops containing a chromosome hybridized to the probe to a subpopulation of microdrops containing a chromosome not hybridized to the probe is determined. In some methods, the probe hybridizes to a nucleic acid segment bearing a mutation and the ratio indicates the proportion of cells in the population bearing the mutation. Such methods are particularly useful for analyzing somatic mutations.

In some methods, an isolated microdrop containing a single chromosome is used to prepare a single chromosomal fragment library. Such a library can in turn be used for preparing probes for a single chromosome, such as painting or reverse painting probes.

Gel microdrops encapsulated biological entities can be stored before or after the hybridization step for a period of at least six months.

The invention further provides methods of diagnosing a disease due to a genetic mutation. Such methods entail obtaining a sample of cells from a patient. A population of chromosomes from the sample in then encapsulated in a population of microdrops. One then contacts the microdrops with a first probe that is complementary to a nucleic acid segment containing the somatic mutation, and a second probe complementary to the chromosome in which the somatic mutation occurs at a site distal to the somatic mutation. The first probe hybridizes to microdrops bearing the chromosome with a somatic mutation and the second probe hybridizes to microdrops bearing the chromosome irrespective whether the somatic mutation is present. One then determines the ratio of microdrops hybridizing to the first probe and hybridizing to the second probe. The ration can then be used to diagnose the existence or prognosis of the disease from the ratio. Such methods are particular useful for diagnosing existence or prognosis of cancer.

The invention further provides methods of chromosome analysis. Such methods entail forming a population of gel microdrops encapsulating a population of nucleic, whereby at least some microdrops in the population each encapsulate a single nucleus. One then contacts the population of gel microdrops with a probe under conditions whereby the probe specifically hybridizes to at least one complementary sequence in at least one chromosome in a nucleus of least one gel microdrop. One then isolates or detects the at least one gel microdrop.

The invention further provides methods of isolating chromosomes. Some such methods entail culturing a population of cells in genistein and colcemid to synchronize chromosomes in metaphase, and isolating chromosomes from the cells. Other methods, which can be used in conjunction or independently of the previously described methods, entail lysing a population of cells to form a lysate. The lysate is then treated with an antibody linked to a magnetic particles, wherein the antibody specifically binds to one or more chromosomes in the cells. Magnetic particles are then isolated from the lysate.

The invention further provides methods of chromosome analysis. Such methods entail forming a population of gel micropdrops encapsulating a population of cells or nuclei, whereby at least some microdrops in the population each encapsulate a single nucleus. One then contacts the population of gel microdrops with a probe under conditions whereby the probe specifically hybridizes to at least one complementary sequence in at least one nucleus in at least one gel microdrop. One then isolates or detects the at least one gel microdrop.

The invention further provides a kit comprising high melting temperature agarose, emulsification equipment, and a label indicating how to use the kit for probe hybridization analysis. Optionally, the kit also includes at least one probe that hybridizes to a nucleic acid.

BRIEF DESCRIPTION OF THE FIGURES

FIG. 3A shows flow sorting of human chromosome 22 following microdrops in situ hybridization using a bcr locus specific probe. FIG. 3B shows sorted chromosomes visualized using fluorescent microscopy.

DEFINITIONS

Figure 1:
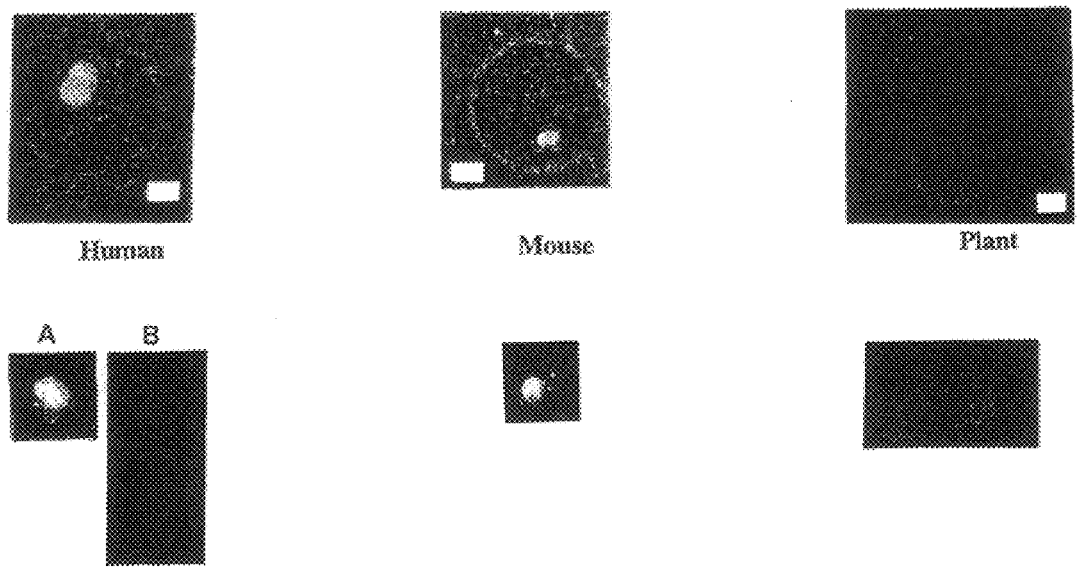
FIG. 1 shows encapsulated and unencapsulated human, mouse and plant chromosomes.

An isolated species means an object species invention that is the predominant species present (i.e., on a molar basis it is more abundant than any other individual species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods).

Polymorphism refers to the occurrence of two or more genetically determined alternative sequences or alleles in a population. A polymorphic marker or site is the locus at which divergence occurs.

DETAILED DESCRIPTION

I. General

The invention provides methods of analyzing populations of nucleic-acid containing biological entities by probe hybridization. For example, the methods can be used to analyze cells, viruses, isolated nuclei or isolated chromosomes. The methods work by encapsulating biological entities in gel microdrops, such that at least some microdrops in a population contain a single entity. The gel droplet provides a stabilization matrix for hybridization and holds hybridized nucleic acids together for subsequent analysis. Encapsulated entities are hybridized with one or more probes. GMDs are easily recovered using low speed centrifugation. Probes can, for example, be designed to hybridize to particular chromosomes or to specific chromosomal loci which are the site of genetic abnormality. After hybridization, the encapsulated entities are detected and/or isolated based on hybridization signal.

The methods allow very large numbers of biological entities to be analyzed simultaneously and can detect entities with rare genotypes from within such populations. For example, the methods can be used to identify rare cancerous cells in a population of normal cells at an early stage in the development of the cancer. Other applications included gene identification, isolating cells expressing a particular gene, preparation of specific hybridization probes, and isolation of pure starting material for DNA sequencing. An additional benefit is that encapsulation in a permeable matrix permits hybridization in free solution, improving the reaction kinetics. A further benefit is that the encapsulation matrix can serve as a repository for a substrate for a reaction catalyzed by an enzyme bound to a probe. Use of chemiluminescent substrates in this manner results in highly sensitive detection.

II. Formation of Droplets

Gel Microdrop (GMD) encapsulation evolved from an interest in studying individual cells (1–11). GMD's provide a defined microenvironment around a biologically entity. The gel does not impede diffusion and allows analysis of large numbers of individual GMDs using flow cytometry, as well as recovery of GMDs of interest using FACS. The number of biological entities encapsulated within each GMD is approximated by Poisson statistics, similar to limiting dilution cloning or petri dish inoculation. To obtain a preparation with a high probability that each GMD contains 0 or 1 initial chromosomes, about 10% of the GMDs should be occupied. GMDs can be prepared by dispersing entities in liquefied gel, such as agarose, into an excess of a hydrophobic fluid to form an emulsion. The emulsion is transiently cooled, causing gelling. Once formed, GMDs are physically distinct and robust and can be removed from the oil into an aqueous medium by low speed centrifugation. Alternatively, GMD's can be formed by passing a mixture of liquefied gel and entities through a pulsating nozzle, such as the printhead of an inkjet printer.

Instrumentation for microdrop formation, the CellSys 100™ Microdrop Maker, is a specially designed emulsifier coupled to a high precision motor available from OneCell Systems, Inc. By varying the rotation speed, type and amount of surfactant, and emulsion viscosity, microdrops ranging from, for example, 2–200 μm can be prepared. Although the Microdrop Maker currently available from One Cell Systems is most efficient for making large numbers of microdrops (e.g., $10^7$), which in turn requires one million biological entities to meet the single occupancy requirement of the microencapsulation procedure, it can be miniaturized for encapsulation of smaller chromosomal preparations. Such is useful for clinical applications, e.g., evaluation of bone marrow samples in which only a small number of cells are present.

Several types of gel can be used for making droplets including agarose, alginate, carrageenan, or polyacrylamide. High melting temperature agarose is preferred for encapsulating larger human and plant chromosomes.

III. Biological Entities

The methods are generally applicable for screening nucleic acids, and any biological entity containing them. Examples of biological entities include cells, organelles, such as nuclei, mitochondria and chloroplasts; chromosomes and fragments thereof, and viruses. Such entities can be from any species including mammals, fish, amphibians, avians, insects, bacteria, eubacteria and plants. Preferred mammals include humans, primates, bovines, and rodents, such as mice, rats and rabbits.

In some methods, biological entities are obtained from a tissue from a human patient. The tissue sample often contains a nonclonal population of cells. Samples can be obtained from any tissue, but blood samples, and samples from tissues from the loci of diseases to which the patient is suspected of being susceptible are preferred. In some methods, cells from primary tissue samples are propagated before analysis. In some methods, biological entities are pooled from more than one individual before analysis. In some methods, biological entities (e.g., chromosomes) are obtained from a homogenous cell line. Cells can be encapsulated and analyzed directly, or nuclei or chromosomes can be isolated from cells for analysis.

IV. Pretreatment of GMD's before Hybridization

Preferably, polymers forming the gel are crosslinked to each other and/or to the biological entity. Preferably, such crosslinking is reversible without damage to the biological entity, thereby allowing the biological entity to be recovered after hybridization and subjected to further DNA manipulations. Such crosslinking assists in preservation of structural integrity of GMD's in the subsequent denaturation step and hybridization steps. Harsh chemical fixation treatments, such as the formaldehyde treatment, used in conventional FISH, are not required. Such fixation treatments form an internal matrix by cross-linking endogenous primary amino groups in a biological entity.

Crosslinked gel microdrops can withstand high temperatures (at least 68°) or concentrations of denaturing solvents such as formamide (e.g., 10, 20, 30, 40 or up to 50% concentration of formamide). Optionally, segments of DNA or RNA can be amplified within the droplets using PCR. A PCR buffer including primers is diffused into droplets, and the droplets are subject to temperature cycling as in a conventional PCR reaction. Irrespective whether amplification is performed, nucleic acids within the GMD's are typically denatured (e.g., by treatment with alkali, heat, formamide or other chemical denaturant) before performing the hybridization step.

V. Probes

Probes are designed to hybridize with selected segment(s) in the nucleic acids of biological entities being screened. Typical probes are those used in conventional genetic and cytogenetic analyses. In many methods, two or more probes with different binding specifies are used. In some methods, a large population of different probes is used. Typically, probes bear detectable labels. If more than one type of probe is used, the different types sometimes bear different labels.

Some probes used in the methods are locus-specific probes, including allele-specific probes and species-specific probes. Allele-specific probes hybridize to one allele of a gene within a species without hybridizing to other alleles. Similarly, species-specific probes hybridize to a gene from one species without hybridizing to the cognate gene in another species. Some probes used in the method hybridize to a variant form of chromosome associated with disease without hybridizing to a wildtype form of the chromosome found in normal individuals. Some probes are mixtures of probes designed to hybridize to one chromosome from an individual or species without hybridizing to other chromosomes. For example, a population of probes can be designed to hybridize to the human X chromosome without hybridizing to other human chromosomes. Some probes are mixtures designed to hybridize to several different chromosomes. For example, a mixture of probes can be designed to hybridize to each of the human chromosomes. Some probes hybridize to satellite or repeat regions within chromosomes. Some probes hybridize to centromeric regions of chromosomes.

Some probes are chromosome painting probes or reverse chromosome painting probes. Chromosome painting probes are a collection of probes designed to hybridize to a segment of a chromosome. Microscopic analysis of a chromosome hybridized to such probes shows a contiguous segment of label if the entire segment of the chromosome is present. If the segment is interrupted by a substitution, deletion or insertion, a gap appears in the pattern of label, signifying the presence of a genetic abnormality. Reverse chromosome painting probes are designed to hybridize to a contiguous segment of a chromosome bearing a known mutation. Microscopic analysis of a chromosome bearing such a mutation hybridized to reverse painting probes shows a contiguous segment of label.

Reverse chromosome painting has been useful for determining the origin of de novo unbalanced chromosome duplications and the extent of deletions or balanced translocations (20). However, aberrant chromosomes are often difficult to distinguish in conventional FISH methods because the derivative chromosome can overlay normal chromosomes. Use of reverse chromosome painting after separation of chromosomes by flow cytometry eliminates this problem.

Some probes are designed to bind to mRNA within a cell. Such probes can be designed incorporating a segment from the antisense strand of a cDNA sequence.

Probes are typically nucleic acids, and can be RNA, DNA or PNA. Probes can also be antibodies or other proteins with capacity to bind to DNA in a sequence-specific manner.

VI. Labels

Probes are typically labelled. The labels used permit separation based on flow cytometry and/or microscopic visualization of label. In some methods, probes are labelled with fluorescent label such as fluorescein. If multiple probes are used simultaneously the probes can be labelled with different fluorescent molecules emitting at different wavelengths to allow differential detection.

In some method, the signal from a label attached to a probe is amplified by binding molecules bearing secondary labels to the label. For example, a hybridized probe labelled with fluorescein can be incubated 15–30 min with rabbit anti-fluorescein IgG conjugated with biotin (Accurate Chemical & Scientific). After washing with PBS buffer, GMDs are incubated for 15–30 min with avidin-FITC or avidin-phycoerythrin (Sigma, St. Louis, Mo.). Because, on average, each anti-fluorescein is labeled with five biotin molecules and each biotin molecule can bind 2–4 avidin molecules, a 10–20 fold amplification in signal is obtained.

In some methods, probes are labelled with an enzyme that catalyzes conversion of a substrate to a secondary label that allows separation and/or visualization of GMD'S.

In some methods, as well as being hybridized to sequence-specific probes, GMD's are labelled with compounds that binds to any DNA sequence. Such labelling serves to distinguish GMD's containing a biological entity with empty GMD's.

VII. Separation and Analysis of Hybridized GMDs

After hybridization with labelled probes, GMDs can be analyzed on a flow cytometer. In the simplest case, in which a single probe type is used, the flow cytometer counts the number of GMDs bearing a label and the number of GMD's lacking a label. If two different probes bearing different labels are used, the flow cytometer can count GMD's bearing first label only, GMD's bearing second label only, GMD's bearing both labels, and GMD's bearing neither label. In methods employing larger numbers of probes, still further categories of GMD's can be distinguished.

If a probe is directed to a particular sequence (e.g., a specific chromosomal defect), detection of GMD's hybridized to that probe signals that the defect is present in at least some of the biological entities being analyzed. If all GMD's bearing biological entities are labelled with a second label, it is possible to determine a ratio of the GMD's hybridized to the specific probe with all GMD's encapsulating a biological entity. This ratio is the proportion of biological entities in a sample preparation bearing a defect. The methods are sufficiently sensitive to detect rare cells in larger populations, e.g., one cell in 10, 100, 1000, 10,000, 100,000 or 1,000,000. This ratio can be significant in determining the existence or prognosis of a disease. For example, if a sample of a cell is from a tissue suspected of being susceptible to cancer, the ratio of cells bearing a defect associated with cancer to the total number of cells in a sample is a measure of how far the cancer has progressed.

In some methods, GMD's encapsulating chromosomes are hybridized with two different probes which are complementary to segments normally found on different chromosomes but which are translocated into the same chromosome in cancerous cells. In this situation, the ratio of GMD's binding to both probes relative to the GMD's binding to one probe or the other but not both, gives the ratio of cancerous to normal cells in a population.

Optionally, flow cytometry can be followed by FACS sorting to make different classes of GMD's available for further analysis, such as microscopy, or chromosome preparation. Alternatively, gel microdroplets can be labelled with magnetic particles and subjected to magnetic separation (MACS). Magnetic particles can be directly attached to hybridization probes or can be supplied in a form that they specifically bind to hybridization probes.

VIII. Visualization of Hybridized Chromosomes

Encapsulated biological entities can be visualized with or without prior flow cytometry and FACS separation to determine the location(s) at which probe has bound. Analysis after flow cytometry and FACS separation can be advantageous because at that stage one has a relatively pure population of biological entities that has hybridized to a given probe. Biological entities can be visualized by microscopy, digital image analyzing, scanning cytometry, photon counting or ccd. Visualization is useful for analyzing hybridization of chromosome painting probes or reverse chromosome painting probes. Visualization is also useful for determining chromosomal copy number within a cell, and hence the existence of chromosomal deletions or duplications. For biological entities containing multiple chromosomes (e.g., cells and nuclei) visualization can also be used to distinguish between two different probes binding to separate chromosomes or to the same chromosome. As noted, such analysis is useful in identifying some forms of cancer.

Biological entities are preferably immobilized on microscope slides or the like for visualization. For example, placing a small quantity (10 $\mu$l) of GMDs dispersed in substrate on the glass slide with a cover slip sufficiently immobilizes GMDs permitting reliable detection of emitted light.

Digital imaging has become an indispensable tool for biological research due to several advantages when compared to the human eye. The higher sensitivity imaging detector enables one to visualize very low light objects which are not detectable by the unaided human eye. The spectrum sensitivity of the human eye is limited from 400 to 700 nm. In contrast, the spectrum sensitivity range of imaging detectors is more broad, and signals from the range of x-ray to infrared can be detected.

A charged-coupled device (CCD) camera providing exposures ranging from seconds to minutes and has advantages for detecting low light levels. These cameras are coupled to a microscope; then digital images are collected with the help of appropriate instrumentation. For low light applications, there are two types of CCD cameras available. The first is the Intensified CCD (ICCD) camera which uses an Image Intensifier and a CCD camera. The Image Intensifier enhances low light image and the intensified image is projected onto a CCD camera through relay optics, such as a relay lens, enabling one to visualize low light image undetectable using a CCD alone. The second is a Cooled CCD (CCCD) camera which uses a similar CCD chip for high light imaging. The CCCD reduces camera noise by cooling and slowly reading out the signal. The reduction of noise enables one to visualize a low light image ordinarily buried in the noise of a regular CCD camera.

IX. DNA Isolation

The gel environment preserves chromosomal DNA molecules in intact form. DNA in encapsulated chromosomes containing GMD's can be cleaved to fragments in situ with restriction enzymes. For large fragments, partial digestion is preferred. DNA fragments can then be released from drops by digesting the gel matrix. For example, if the matrix is agarose, the gel matrix can be digested with the enzyme agarose. Large fragments are then cloned into vectors such as YACs, BACs or PACs. Libraries from purified human chromosomes preparable by the above methods are useful for sequencing or mapping the human genome and for positional cloning. Pure sorted chromosomes are also useful as a source of chromosome painting and reverse chromosome painting probes. Such probes can be prepared by amplification of chromosomal DNA using degenerate primers.

X. Storage of Encapsulated Biological Entities

Encapsulated biological entities such as chromosomes can be stored for an hour, a day, a week, a month, six months, a year, two years or five years or more without visible degradation of nucleic acids. Stored chromosomes can eventually be used for isolating specific genes, for preparing PCR probes, and for generating high quality starting material for DNA sequencing, or for clinical analysis.

XI. Applications

The above methods can be applied to diagnosing the presence, susceptibility, or prognosis of diseases associated with genetic defects. The methods are particularly useful in diagnosing and monitoring diseases due to genetic defects that are only present in a subpopulation of cells, such as defects arising from somatic mutation. Examples of such diseases associated with genetic defects include autoimmune diseases, inflammation, cancer, diseases of the nervous system, and hypertension. Some examples of autoimmune diseases include rheumatoid arthritis, multiple sclerosis, diabetes (insulin-dependent and non-independent), systemic lupus erythematosus and Graves disease. Some examples of cancers include cancers of the bladder, brain, breast, colon, esophagus, kidney, leukemia, liver, lung, oral cavity, ovary, pancreas, prostate, skin, stomach and uterus.

Many cancers arise due to mutations in rare subpopulations of cells. Cancers develop and progress through the accumulation of genetic abnormalities at critical loci (34, 35). These abnormalities may involve alterations of one or a few bases of DNA, deletions ranging from sub-microscopic to whole chromosomes, duplications or higher-level amplifications of chromosomal regions, or rearrangements producing abnormal juxtapositions of DNA sequences (36). In some case, such as the abl-bcr fusion on the original Philadelphia chromosome, specific translocations are associated with activation or modification of human proto-oncogenes (37, 38). Similarly, Ewing's sarcoma is associated with a translocation involving the EWS gene on chromosome 22. Determination of the proportion of cancerous cells in a tumor allows grading of the tumor for improved diagnosis, prognosis and treatment planning. The ratio can also be valuable in evaluating both the adequacy of surgical margins and the presence of microscopic metastases in bone marrow or other sites.

The methods are also useful for diagnosing the presence of latent viruses. For example, some viruses, such as Herpes viruses and retroviruses, integrate into genomic DNA of some cells within the body and remain dormant until activated. Analysis of a tissue sample from a patient having or suspected of being infected with such a virus can identify the percentage of cells infected with the virus and the copy number of the virus in different cells. Such information is useful in diagnosing the presence of virus, the severity of infection and the recommended course of treatment. Presence of a virus can be detected using a probe designed to hybridize either to viral genomic nucleic acid or to viral mRNA, or both. The methods can similarly be used to determine copy number of viral mRNA in cells from the patient. Such information can be useful in monitoring the progress of disease, for example, in response to treatment with a drug.

The methods are also useful for determining allelic frequencies in a population, and correlating such frequencies with a phenotype. For example, cells taken from a population of individuals can be pooled, and screened to determine the frequencies of different allelic forms of a gene. If the population has a common phenotype (e.g., a disease), a correlation can be performed to determine whether the presence of one of the allelic forms is statistically associated with the phenotype.

The methods are also useful for identifying cell types expressing a gene of interest. For example, if a new gene of unknown function has been discovered, one can design a probe that is complementary to an exonic segment and optionally, to segments in successive exons. Hence, the probe can hybridize to mRNA expressed from the gene. A population of cells is obtained from different tissues of an individual, and the cells are screened for hybridization to the probe. Cells hybridizing to the probe express the gene. The nature of cells expressing a gene provides valuable information concerning the function of the gene.

Similar methods can be used to clone a cDNA if only a portion of the coding sequence is known. The portion of known sequence is used to design a probe. A population of different cells is then encapsulated and hybridized with the probe. Cells are then separated according to extent of expression. Cells showing the highest level of expression provide a suitable source material from which to clone the cDNA.

The methods are also useful for comparing or monitoring the expression of a given gene or gene(s) in different cell types. A probe is designed to hybridize to a mRNA transcript of each gene of interest. Optionally, different probes can bear different labels. Probes are then hybridized with mRNA in a microdrop encapsulated cell population, which typically includes cells of different types. The extent of hybridization of each cell with each probe is then determined. Optionally, cells hybridizing with a particular probe at significantly above or below average levels are isolated and cell type determined, allowing correlation between cell type and expression level. Optionally, different cell types in a population can themselves be labelled with reagents that specifically bind to a particular cell type. For example, a particular cell type can be labelled using an antibody that binds to a receptor specific to the cell type. Microdrops are then analyzed for both cell type labels and probe labels, thereby facilitating comparison of expression levels of particular mRNA species between the cell types that have been specifically labelled.

The methods are also useful for preparing isolated chromosomes. As noted, isolated chromosomes are useful for e.g., positional cloning studies and for preparing probes.

XII. Kits

The invention also includes kits for the practice of the methods of the invention. The kits comprise equipment and/or reagent(s) for making gel microdrops and optionally, probe(s) for performing hybridization to encapsulated nucleic acids. Examples of equipment include a CellSys 100™ Microdrop Maker and components thereof, an instrument providing a pulsating novel, such as an inkjet printer, and a vortexer. Examples of reagents include chemicals for making a gel, such as agarose or acrylamide, cross-linking reagents, denaturing agents, and hybridization buffer. The kits can also include label(s) and other chemicals to amplify label signal. The kits usually include labelling or instructions indicating the suitability of the kits for performing hybridization in gel drops and/or flow cytometrix analysis. The term "label" is used generically to encompass any written or recorded material that is attached to, or otherwise accompanies the kit at any time during its manufacture, transport, sale or use.

EXAMPLES

1. Encapsulation, Hybridization and Screening of Chromosomes, and Stability of Encapsulated Chromosomes Materials and Methods Cell Lines and Culture Conditions Human chronic myelogenous leukemia, K-562, human acute lymphocytic leukemia, REH (American Type Culture Collection, Rockville, Md.), and mouse fibroblast, Mus Spretus C1-5A (Los Alamos National Laboratory, Los Alamos, N. Mex.) cells were grown in RPMI 1640 medium supplemented with 10% fetal bovine serum at 37° C. in the presence of 5% $CO_2$. Normal human lymphoblast cells GM130 (NIGMS Human Genetic Mutant Cell Repository, Coriell Institute for Medical Research, Camden, N.J.) were grown under identical conditions, except that RPMI 1640 medium was supplemented with 15% heat inactivated fetal bovine serum.

Source of Plant Chromosomes Plant chromosomes from the field bean *Vicia faba*, (from J. Dolezel, Institute of Experimental Botany, Olomouc, Czech Republic), were isolated from root meristems after cell cycle synchronization with hydroxyurea and metaphase accumulation with amiprophos methyl (21).

Mitotic Cell Preparation Mouse C1-5A cells (an adherent cell line) undergoing logarithmic growth were treated with 0.2 µg/ml colcemid (Sigma, St. Louis, Mo.) for 12–15 hours. Mitotic cells, which become less adherent, were shaken-off and resuspended in hypotonic solution (55 mM KCl). Human K-562 cells undergoing exponential growth were treated with 60 µM genistein (Sigma) for 24 hours to synchronize growth (23). Cells were then pelleted and washed once with Hank's balanced salt solution (Sigma). Fresh media containing 0.1 µg/ml of colcemid was added and cells were grown for an additional 24 hours. After counting, cells were pelleted by centrifugation (100 g for 10 min at 4° C.) and resuspended in hypotonic solution (75 mM KCl). Human REH cells were grown to stationary phase, to synchronize growth, then were left for 2 days. Cells were harvested by low speed centrifugation and grown in fresh media containing 0.1 µg/ml colcemid for 24 hours. After pelleting, cells were resuspended in hypotonic solution (75 mM KCl).

Chromosome Isolation Human and mouse chromosomes were isolated using the polyamine method (31,32), with minor modifications. Approximately $2 \times 10^7$ cells were swelled in 10 ml of hypotonic solution either for 30 min (human REH) or for 1 hr (human K-562 and mouse C1-5A cells) at room temperature. After swelling, cells were pelleted by 5 min centrifugation at 40 g, and gently resuspended in 0.1 ml of fresh hypotonic solution. Two ml of chromosome isolation buffer (CIB; 15 mM Tris-HCl, 80 mM KCl, 20 mM NaCl, 2 mM EDTA, 0.5 mM EGTA, 0.2 mM spermine, 0.5 mM spermidine, pH 7.2) supplemented with 0.1% (v/v) 2-mercaptoethanol and 0.2% (v/v) Triton X-100 was added and solutions were mixed by brief (10 sec) vortexing. Tubes were kept at 0° C. for approximately 10 min. C1-5A cells were passed through a 25 gauge needle until chromosomes were released, as monitored by fluorescence microscopy. Nuclei and cellular fragments were removed by three successive 5 min centrifugations at 40 g. The top two thirds of the supernatant, after the final centrifugation, was kept at 4° C. for 16 hr. The supernatant was then carefully decanted to avoid disturbing the settled chromosomal pellet. Chromosomes were resuspended in 0.2 ml of CIB and aggregates were pelleted by centrifugation for 5 min at 40 g. Chromosomes were either stored in CIB or immediately encapsulated in agarose gel microdrops (GMDs).

Chromosome Encapsulation The chromosome/agarose mixture (2.3% Type XII agarose; (Sigma) 0.1% Triton X-100 (Sigma) containing $10^6$ chromosomes/0.55 ml) was prepared by melting the agarose in CIB at 100° C., cooling the agarose to 58° C., and adding 100 µl of chromosome suspension and 50 µl of 11% (v/v) Triton X-100 (pre-warmed to 58° C.) to 0.4 ml of melted agarose. The mixture was held at 58° C. for 5 min and added dropwise to 15 ml of CelMix™ 200 emulsion matrix (One Cell Systems, Cambridge, Mass.) which was also pre-warmed to 58° C. GMDs were generated with a CellSys100™ Microdrop Maker (One Cell Systems, Cambridge, Mass.) equipped with a 1.6 cm blade using successive rotor speeds of 1,500 rpm for 1 min at 20–25° C., 1,500 rpm for 1 min at 0° C., and 1,500 rpm for 5 min at 0° C. GMDs were separated from the emulsion matrix by centrifugation at 350 g for 10 min. The encapsulated chromosome-containing pellet was washed twice with 13 ml of CIB, re-pelleted by centrifuging 5 min at 250 g, and stored at 4° C. in 10 ml of the same buffer.

Chromosome Staining Encapsulated chromosomes were stained with propidium iodide (0.4 µg/ml) for microscopic examinations and with 7-actinomycin (7AAD) at the same concentration, both from Sigma, for flow cytometry.

Hybridization Probes LSI™ 22q (bcr-locus specific, Vysis, Downers Grove, Ill.), which hybridizes to a 300 kb region of the bcr gene on chromosome 22, was used. This probe was directly labeled with Spectrum Green™ (fluorescein). After labeling, the probe size distribution ranged from 50–500 nt. The DNA probe was denatured at 95° C. for 5 min before hybridization.

Microdrop In Situ Hybridization (MISH) of Human Chromosomes Encapsulated chromosomal DNA was denatured in 0.1 N NaOH, 50% (v/v) ethanol for 1.5 min. GMDs were washed once in 0.5 M sodium carbonate, pH 10.2. After denaturation, the hydroxyl groups in the agarose microdrops were mildly crosslinked with 5 µM divinylsulfone by incubating 30 min at room temperature. Excess reactive groups from divinylsulfone were blocked with 2% (v/v) 2-mercaptoethanol for 30 min in 40 mM Tris-HCl, pH 8.0. GMDs were then washed with 2×SSC (0.15M NaCl, 0.015M sodium citrate).

100 µl (approximately $2 \times 10^5$) of human chromosomes encapsulated in GMDs was hybridized with 2.0 µl of the denatured probes (probe concentration was proprietary for the manufacturer) in a hybridization mixture (2×SSC, 10% (v/v) dextran sulfate, 50 µg/ml salmon sperm ssDNA for 16 hours at 68° C. After hybridization, non-specifically bound probe was removed by incubating GMDs with 1.0 ml 0.4×SSC at 72° C. for 5 min (LSI/22) and washing twice with 0.4×SSC at room temperature. Cot DNA was added to prevent non-specific hybridization to repetitive sequences.

Microscopy and Digital Image Analysis The integrity of chromosomes after fluorescent staining or MISH was checked visually using an Olympus BH-2 microscope (40× SPlan 0.4 objective or phase contrast A40 PL 0.65 objective) equipped for epifluorescence with appropriate filters for fluorescein and 7AAD.

Flow Cytometric Analysis After staining or MISH, encapsulated chromosomes were analyzed using a FACS Vantage flow cytometer (Becton Dickinson Immunocytometry Systems, San Jose, Calif.) equipped with a standard 100 $\mu$m nozzle. LYSYS II Ver.2.0 software was used for data analysis. To remove large particles, the GMDs were sieved through a 53 $\mu$m nylon mesh (Small Parts Inc., Miami Lakes, Fla.). For flow cytometry analysis, a concentration of microdrops not exceeding $2 \times 10^5$/ml was used. Forward and side scatter signals were analyzed on a log scale and examined in scatter plot format, permitting identification of and gating on GMDs. 7ADD fluorescence was used to identify GMDs containing encapsulated chromosomes. To identify 7ADD, an argon laser with a 356 nm spectral line was used. To identify chromosomes which hybridized to the Spectrum Green™ labeled probe, fluorescein (FITC) intensity was measured. For measuring FITC fluorescence, an argon laser with a 488 nm spectral line was used.

Fluorescence Activated GMD Sorting Encapsulated chromosomes were sorted using a FACS Vantage fluorescence activated cell sorter (Becton Dickinson) adapted with a macrosort option. The sheath pressure was set at 2 psi with a sample differential of 1 psi. A large diameter sample line was used to avoid clogging. The GMD samples were sieved through a 53 $\mu$m mesh before sorting. Sorting speed was in the range of 50 FITC-labeled chromosomes/sec. Sorted GMD-encapsulated chromosomes were pelleted by low speed centrifugation and taken up with 20 $\mu$l of Antifade solution (Oncor, Gaithersburg, Md.), diluted 1:1 with CIB and analyzed using a fluorescence microscope.

Digestion of Denatured Encapsulated Chromosomal DNA with HindIII Encapsulated chromosomes were denatured, as previously described, washed with 40 mM Tris-HCl, pH 8.0 and subsequently digested with Proteinase K (2mg/ml) supplemented with lithium dodecyl sulfate (1%) in CIB for 12 hours at 50° C. Chromosomes were then washed three times with a 200-fold excess of CIB and two times with 20-fold excess of HindIII digestion buffer (50 mM NaCl/10 mM Tris-HCl, pH 8.0/10 MM $MgCl_2$). Digestion of encapsulated chromosomes was done using 20 units of HindIII (Gibco-BRL) in a reaction volume of 50 $\mu$l for 90 min at 37° C. Gel loading buffer was added and samples were electrophoresed as described below.

Gel Electrophoresis of Chromosomal DNA Both free and encapsulated chromosomes were treated with proteinase K and lithium dodecyl sulfate as described above for three hours at 50° C. Gel-loading buffer (6×0.25% bromphenol blue, 0.25% xylene cyanol FF, 30% glycerol) was added and samples were electrophoresed on 0.8% SeaKem Gold (FMC BioProducts, Rockland, Me.) agarose in TAE buffer (0.04 M Tris-acetate, 1 mM EDTA) at 56 volts for 2–6 hours. Propidium iodide was present in the gel (0.5 $\mu$g/ml) and in the electrophoresis buffer (0.05 $\mu$g/ml) during electrophoresis. 0.25 $\mu$g of lambda DNA or 1.0 $\mu$g $\phi$X174 DNA cut with HinFI (Gibco-BRL) was used as a standard.

Chromosome Storage and Recovery Free and encapsulated chromosomes were kept at 4° C. for up to 6 months in CIB. Agarose (from *Pseudomonas atlantica*, Sigma) was used to digest GMDs to recover chromosomes of interest. Encapsulated chromosomes were pelleted, resuspended in phosphate buffered saline solution, pH 7.0 (Sigma), and agarose (30 units per 1000 GMDs) was added. This suspension was incubated at 40° C. for two hours, treated with proteinase K as described above, and chromosomal DNA was analyzed by gel electrophoresis.

Results

FIG. 1 shows encapsulated and unencapsulated human, mouse, and plant chromosomes. Encapsulated chromosomes appear visually more compact than unencapsulated chromosomes, with narrow centromeric regions and tightly bound chromatid extensions. The centromeric region of encapsulated chromosomes appear physically unseparated, which would be an indication of chromatid loss. Interestingly, encapsulation of intact plant chromosomes, which are approximately 3 times larger than human chromosomes, was also successfully performed using this procedure.

Figure 2:
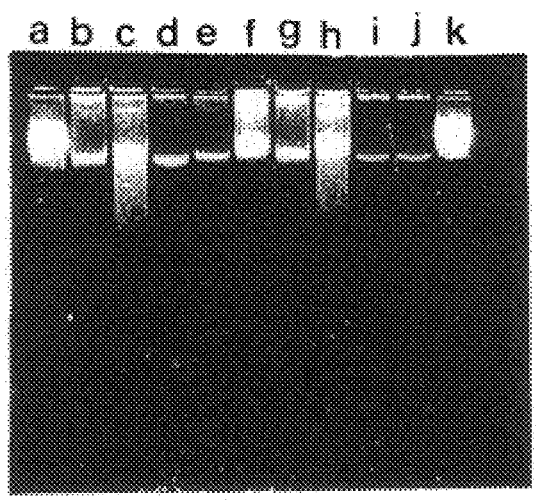
FIG. 2 shows gel electrophoresis of chromosomal DNA. Unencapsulated, freshly isolated chromosomes: b-mouse, e-human K-562, g-human REH; Unencapsulated chromosomes one month after isolation: c-mouse, f-human K-562, h-human REH; Encapsulated chromosomes stored for 6 months: d-mouse, i-human K-562, j-human REH; lambda DNA (0.1 µg) used as a control: a,k.

Stability of Encapsulated Chromosomes To assess the long term stability of encapsulated chromosomes, we examined DNA fragmentation using gel electrophoresis. As depicted in FIG. 2, no DNA fragmentation was found by electrophoretic analysis, even 6 months after encapsulation. In contrast, one month after isolation, DNA from unencapsulated human and mouse chromosomes has a smeared banding pattern, indicative of DNA fragmentation due to nuclease cleavage. This result indicates that encapsulated chromosomal DNA remains intact and can be used for preparing chromosome-specific libraries. Intact isolation and long term stability of high quality, high molecular weight DNA will be a major convenience for researchers and an innovation for sample storage for clinical use.

In Situ Hybridization of Encapsulated Chromosomes An important improvement was development of a matrix crosslinking method which allowed use of up to 50% formamide and temperatures as high as 95° C., necessary for reproducible hybridizations. The agarose hydroxyl groups were mildly crosslinked with divinyl sulfone. Although this procedure also partially crosslinks chromosomal DNA to the agarose matrix, because this process is reversible at pH 10, DNA can be released from GMDs after MISH, which is important for eventual construction of chromosome-specific libraries.

Using a FACS Vantage both for flow cytometric analysis and cell sorting, dual-parameter dotplots were produced by plotting FITC-fluorescence, which was detecting probes hybridized to the chromosomes versus 7AAD fluorescence, which as a general DNA stain was used to detect all chromosomes. FIG. 3A shows flow sorting of human chromosome 22 following microdrops in situ hybridization using a bcr locus specific probe. Chromosomes were counterstained with 7-amino-actino-mycin (Vysis, Downer's Grove, Ill.). Chromosomes were counter-stained with 7AAD. R1 includes high FITC, low 7AAD fluorescence specific for gel microdrops containing chromosome 22. The scattergram also display empty GMDs, encapsulated chromosomes, and noise. FIG. 3B shows sorted chromosomes visualized using fluorescent microscopy. The hybridization signal is depicted in green (FITC) color. Hybridization signals were amplified using the TSA method, which provides a 10–100 increase in signal intensity.

Figure 4:
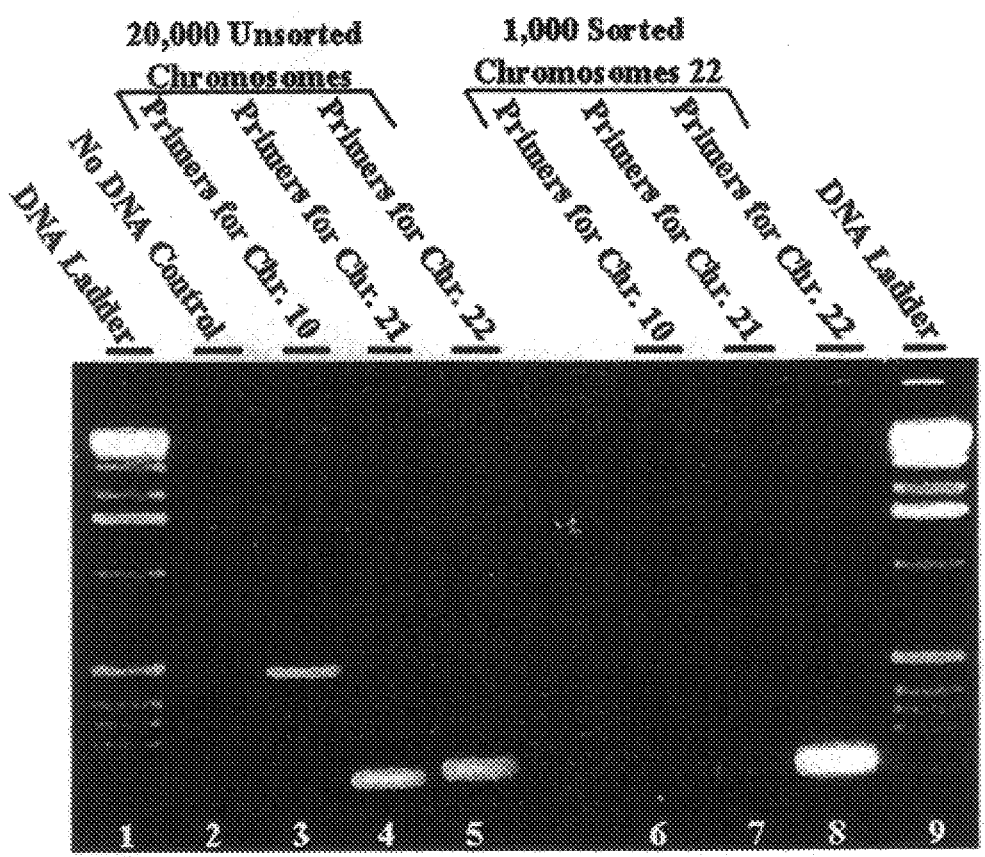
FIG. 4 shows purity of chromosome 22 after sorting measure by the polymerase chain reaction using primer sets specific from chromosomes 10, 21 or 22.

FIG. 4 shows purity of chromosome 22 after sorting measure by the polymerase chain reaction using primer sets specific from chromosomes 10, 21 or 22. Amplification results for each primer set were compared using unsorted and sorted chromosome populations. Unsorted chromosomes generated specific amplicons for each primer (lanes 3–5). Sorted chromosome 22 showed no contamination with chromosome 10 (lane 8 vs. 60 and were less than 1% contaminated with chromosome 21 (lane 8 vs. lane 7).

Recovery of Encapsulated Chromosomes We determined that after recovering chromosomes from agarose microdrops, DNA was not fragmented, even 6 months after encapsulation. We also tested the integrity of DNA after digesting microdrops with agarase and found that the electrophoretic pattern was the same as that of untreated encapsulated chromosomes used as controls. These observations show that after release from gel microdrops, encapsulated chromosomes will be a convenient source of high quality DNA for molecular genetics studies.

Figure 5:
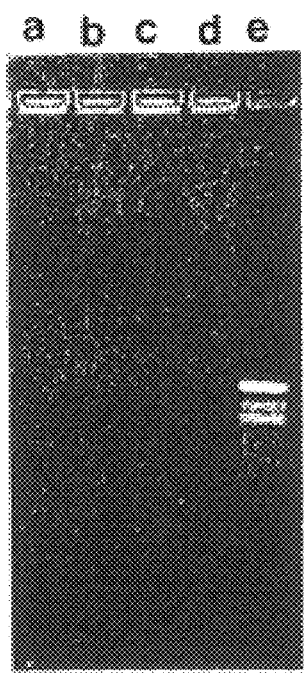
FIG. 5 Restriction digestion of encapsulated chromosomes.

Digestion of Denatured Encapsulated Chromosomes A major concern for eventual use of sorted chromosomes to construct chromosome-specific libraries was that digestion of chromosomal DNA with restriction enzymes, which is necessary for cloning large DNA fragments (>100 kb) into BAC libraries, would be impossible because denaturation would destroy the DNA secondary structure. To address this concern, we tested the hypothesis that brief alkaline use would only partially denature the DNA and that subsequent digestion with proteinase K at 50° C. in low salt buffer overnight would restore double strandedness, thus making specific enzyme digestion possible. Human chromosomes isolated from the GM 130 cell line were digested with proteinase K and cleaved with HindIII. The electrophoretic result depicted in FIG. 5 shows that the restriction endonuclease HindIII cleaved restored DNA and generated typical sized fragments, demonstrating that MISH treated chromosomes can be used for library construction.

Example 2

Construction of Chromosome-Specific BAC Libraries

A major unrealized goal of fluorescence in situ hybridization assays has been the use of flow cytometry to isolate specific chromosomes for library construction. Prior to development of the MISH method, after hybridization, only a small fraction of chromosomes remain intact and free in suspension. Without the protection gained using the agarose microspheres, most chromosomes are clumped or fragmented, making them largely unsuitable for flow cytometric analysis (27). We have shown not only that we can hybridize and flow sort encapsulated chromosomes, but also that alkaline-denatured chromosomes can be digested with restriction endonucleases. As a result of this finding, we propose construction of chromosome-specific libraries. Human chromosome 21 was chosen because it is often difficult to identify and sort using conventional dual fluorescent staining since it is small and indistinguishable in the presence of cellular debris (29). The second BAC library will be constructed using human chromosomes 9, which belongs to the group of chromosomes not resolvable by conventional dual fluorescent staining because of its similarity in size to several other chromosomes (13). Chromosome libraries are constructed using the steps below.

Sort MISH-labeled chromosomes
↓
Remove hybridized probes
↓
Digest sorted chromosomes with proteinase K in low salt buffer
↓

-continued

Digest chromosomal DNA with restriction enzymes
↓
Ligate DNA fragments into BAC vector
↓
Electroporate ligated product into E. coli host
↓
Screen transformants for chromosome-specific inserts Example 3

Use of MISH-sorted Chromosomes for Reverse Chromosome Painting

The development of in situ hybridizations with flow sorted chromosome libraries (25,26), combined with non-isotopic signal detection (30), has become a powerful approach for rapidly analyzing human chromosomal aberrations, such as aneuploidy and translocations. These techniques, termed chromosome painting, are becoming widely used in clinical cytogenetics. However, small rearrangements, additions, or deletions are not detectable using conventional chromosome painting, but these aberrations are detectable by reverse chromosome painting, which is performed using a probe prepared from aberrant chromosomes. A method of using MISH-sorted chromosomes is depicted below.

Sort MISH-labeled aberrant chromosomes
↓
Deproteinize sorted chromosomes
↓
First round of chromosomal DNA PCR amplification
↓
Biotin-label probe production by a second round of PCR amplification
↓
Use probe in FISH painting of normal chromosome metaphase spreads Example 4

Detection of the Philadelphia Chromosome

The Philadelphia chromosome is a shortened chromosome 22 that results from a balanced translocation between chromosomes 9 and 22 with the translocation breakpoints at 9q34 and 22q11. As a result of this translocation, most of the abl oncogene, located on chromosome 9, is juxtaposed to part of the bcr gene, located on chromosome 22, creating a new bcr-abl gene fusion (40, 51, 52, 53, 54). This gene fusion encodes an abnormal protein with strong tyrosine kinase activity compared with the weak tyrosine kinase activity of the normal abl protein. The abnormal tyrosine kinase produced from bcr-abl causes increased cell proliferation and contributes to leukemogenesis by unknown cellular pathways.

Translocations such as bcr/abl are currently detected by cytogenetic examination of metaphase chromosome preparations prepared from bone marrow cultures. Although this method is adequate to detect most chronic myelogenous leukemia cases (CML) in which $Ph^1$-positive chromosomal translocations are visible after banding due to the size difference in metaphase spreads, in acute lymphoblastic leukemia (ALL), cytogenetic examination is successful in only 65–80% of the cases, depending on the experience of each laboratory (55). The lower yield in ALL is the result of the following factors. First, many ALL patients have inaspirable bone marrows, so no cells are available. Second, lymphoblasts can be difficult to culture, so there is little enrichment of leukemia cells. And third, the percentage of $Ph^1$ carrying cells in a sample may be as low as 30%, in contrast with CML in which virtually 100% of the cancerous cells in the sample carry $Ph^1$. In cases where chromosomal rearrangements are not visible in classical metaphase spreads, which can occur in $Ph^1$-positive chromosomes, both in CML or ALL leukemias, fluorescence in situ hybridization, Southern blot (DNA) analysis, or polymerase chain reaction (PCR) analysis must be performed to detect rearrangements (55).

In CML, Southern blot analysis has been useful in detecting evidence of $Ph^1$ chromosome in patients in whom the cytogenetics are negative despite a clinical presentation of CML (53). This approach is only of limited utility in ALL because only 25–50% of $Ph^1$ chromosome positive ALL patients have M-bcr (Major breakpoint rearrangements). Nearly all M-bcr negative patients have translocation breakpoints in m-bcr (minor breakpoint rearrangements) anywhere in the first intron, which is 70-kb in size, requiring performance of an impractical number of Southern blots in order to adequately investigate this entire region.

The chromosomal breakpoints in CML and acute leukemias may occur over large DNA sequences: 5.8 kb for the bcr region in CML and over 90 kb for the first intron of the bcr 1 gene in acute leukemias. Therefore, PCR amplification of the fusion bcr/abl gene sequences cannot be performed on DNA from patient specimens. All PCR based methods are designed to amplify and detect the abnormal fusion of mRNA (RT PCR). The design of these methods takes advantage of the fact that mRNA sequences are much shorter, lacking intron sequences. Assuming primers can be designed to amplify short stretches of mRNA specific for particular translocation (currently available for $Ph^1$ fused mRNA), amplified target can be detected after hybridization with specific probes followed by gel electrophoresis and Northern blotting. The size of bcr/abl fused mRNA for different patients varies within certain ranges for CML and acute leukemia breakpoints, but the same size fusion mRNA is characteristic for each malignant clone and can be monitored for each patient over the clinical course of the leukemia.

An advantage of using mRNA as a target for PCR amplification is that mitotic cells are unnecessary. The practical limit of sensitivity of detection is approximately 1 malignant per 10,000 non-malignant cells. While the exquisite sensitivity of PCR could be advantageous in molecular diagnostic testing, its use is troublesome in the clinical laboratory. Contamination with minute amounts of amplified DNA and/or RNA from patient samples or cell line controls, even in the range of 1 to 10 copies, may generate false-positive results. Aerosols and carryover are the main sources of contamination. A potential problem with monitoring the presence of the $Ph^1$ chromosome after chemotherapy or bone marrow transplant by RT PCR is the presence of residual dead leukemia cells with intact mRNA complicating therapeutic assessment.

The MISH technique combined with flow cytometric analysis makes a significant contribution to analysis of translocations. Because metaphase chromosomes are required, only live leukemia cells contribute $Ph^1$ chromosomes for detection. As long as leukemia cells proliferate and reach mitosis, approximately 20 $Ph^1$ positive chromosomes in the presence of 50,000 chromosomes, including those from Philadelphia-negative cells, can be detected in about 5 min. This corresponds to detection of 20 cells with a single copy of $Ph^1$ chromosome, or 10 cells with two defective copies, in an environment of approximately 1,000 cells which are $Ph^1$ chromosome negative (2% leukemia cells present). To improve statistical significance, analysis of 100,000 events can be performed in approximately 10 minutes, provided that metaphase chromosomes are available from both cell types. In contrast, in current FISH procedure using metaphase spreads obtained from bone marrow cultures which have a mitotic index of 10%, one would have to find one Ph-positive spread in the presence of 1,000 Ph-negative spreads, a labor intensive and impractical approach by conventional microscopy.

Materials and Methods

Chromosome encapsulation and hybridization conditions were as described above. The LSI™ bcr/abl DNA probe was used for in situ hybridization. The probe was directly-labeled with SpectrumGreen™/SpectrumOrange™ which was designed to detect translocations between chromosome 9 and 22 (Vysis, Downers Grove, Ill.). This probe detects bcr/abl gene fusions, the molecular equivalent of the Philadelphia chromosome ($Ph^1$), in both metaphase and interphase cells. It can be used to identity bcr/abl gene fusion involving either of the two breakpoint regions (M-bcr and m-bcr) in the bcr gene on chromosome 22. The bcr/abl translocation probe is qualified for use on both cultured lymphocytes and bone marrow cells. The LSI™ probe does not contain repetitive sequences and is composed of an abl probe directly labeled with SpectrumOrange fluorophore and a bcr probe directly labeled with SpectrumGreen fluorophore. The abl probe begins between c-abl exons 4 and 5 and continues for about 200 kb toward the telomere of chromosome 9. The bcr probe begins either between bcr exons 13 and 14 (m-bcr) or between bcr exons 2 and 3 (M-bcr) and extends toward the centromere approximately 300 kb crossing well beyond the m-bcr region. The probe size distribution is within a range of 50–500 nt (after labeling).

After hybridization, chromosomes containing M-bcr/abl gene fusion in Chronic Myelogenous Leukemia (CML) and in Acute Lymphoblastic Leukemia (ALL) can be expected to contain fused orange and green signals in translocated chromosome 22, which are sometimes perceived as yellow. Normal chromosomes 22 should display green signal and normal chromosomes 9 should display orange signal. Hybridized chromosomes that have the m-bcr/abl gene fusion in ALL should contain fused green/orange signal in chromosome 22 and faint green signal not fused with orange signal on chromosome 9 (from the chromosome 22 region between m-bcr and M-bcr that is translocated to chromosome 9).

Results

Chromosome Isolation To increase the yield of human mitotic cells, K-562 cells were synchronized by a novel method using genistein, an isoflavone which blocks the cell cycle at $G_2/M$. An important advantage of genistein for cell cycle synchronization was that it did not appear to penetrate cells and was easily eliminated by washing. After synchronization, growth of K-562 cells was not significantly affected by the presence of colcemid for up to 24 hours, and a high percentage (75%) of cells, therefore, reached mitosis. Use of genistein yielded a ready supply of millions of chromosomes facilitating extensive experimentation with encapsulation and fluorescent in situ hybridization conditions. The method can also be used to isolate chromosomes for other purposes.

Figure 6:
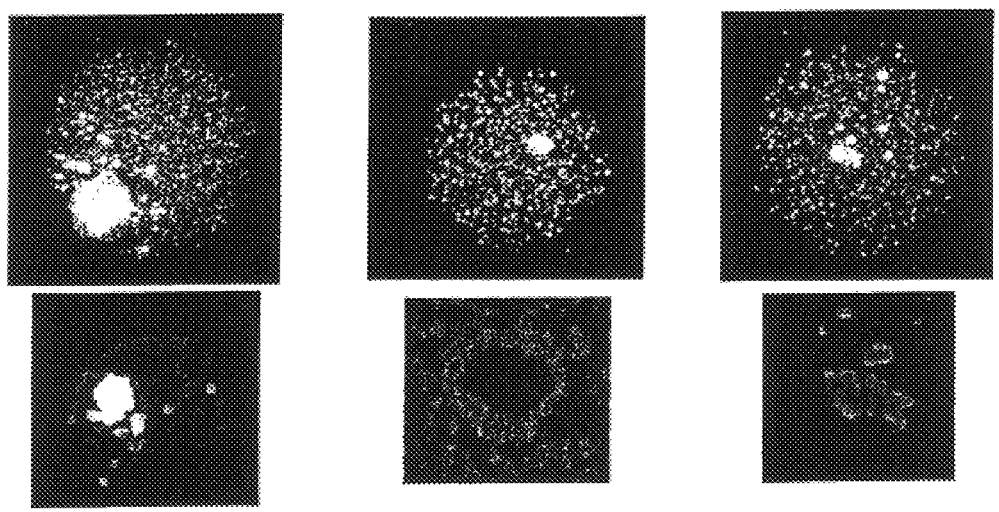
FIG. 6 detection of translocated chromosome 22 left chromosome 9 middle, and translocation-free chromosome 22 right by MISH are shown.

In FIG. 6, detection of translocated chromosome 22 left chromosome 9 middle, and translocation-free chromosome 22 right by MISH are shown. Translocated chromosome 22 is identifiable by the presence of both green and red colors on a background of a blue colored whole chromosome. Fused red and green signals may be perceived as yellow (bottom left of FIG. 6). This yellow color also represents fused bcr/abl gene (translocated chromosome 22). Translocation-free chromosome 22 is detectable by the presence of single green color and chromosome 9 by the presence of single red color. Digital images created by a CELLscan digital image system with Exhaustive Photon Reassignment (EPR), which was available through collaboration, are presented here, but a fluorescence microscope equipped with a triple bandpass filter for DAPI, fluorescein and rhodamine was adequate to identify translocations in Philadelphia[1] chromosome.

Example 6

Analyzing Encapsulated Human Nuclei Using Microscopy and Flow Cytometry

Analyzing MISH signals in nuclei provides improved contrast relative to MISH detection in chromosomes. Moreover, MISH analysis of nuclei can be performed in cases where cell proliferation is difficult or impossible. The applications are numerous and include detection of: translocations, deletions, monosomies or trisomies for diagnostic and prognostic analysis of aberrations. This method can also be used in research applications including gene amplifications and gene mapping. In this example, we use human nuclei with deleted chromosome 3 as a model system. This genetic defect presents numerous clinical symptoms in affected people including mental retardation and multiple congenital anomalies.

Isolation of Nuclei

Nuclei are isolated from human lymphoblastoid cell line GM11428 (NIGMS Human Genetic Mutant Cell Repository, NIH, Bethesda, Md.). HL-60 cells are a source of normal nuclei (control) with no deletions in any chromosome. Cells in logarithmic phase of growth are collected and swelled in hypotonic solution. (75 mM KCl) for 1 hour. Cells are then pelleted by low speed centrifugation and resuspended in 2-mercaptoethanol-free CIB buffer (1 million cells/ml). Triton X-100 is then added to obtain final concentration of 0.2%. Nuclei released from cells are kept in this solution for 1 hour at 4° C., then pelleted by centrifugation at 100×g and resuspended in original cell volume of the same buffer and re pelleted. Finally, nuclei are resuspended at a concentration of 10 million nuclei per ml of 2-mercaptoethanol-free CIB buffer.

Encapsulation of Nuclei

Encapsulation of nuclei is performed essentially as described previously for chromosome encapsulation. However, GMD size can be adjustment from 25–35 to 45–55 μm to account for the larger size of nuclei by modification of blade speed during the emulsification process.

Example 7

Improved Method of Chromosome Isolation

Chromosomes can be synchronized in metaphase by culturing cells from which chromosomes are to be isolated with the flavonoid genistein together with colcemid, which is commonly used to block the cell-cycle at metaphase. This procedure yields a mitotic index of about 75%: (i.e., three out of four cells yielded metaphase chromosomes).

Chromosomes are released from cells by hypotonic treatment. Quantitative release of chromosomes requires at least some physical shearing force, such as vortexing or passage through a gauge needle, and generate some cell debris. After chromosome release, nuclei are removed by low speed centrifugation to remove nuclei. To remove proteins, chromosome lysates are then dialyzed in a Slide-A-Lyzer™ (Pierce, Rockford, Ill.), which has a large pore membrane (100,000 molecular weight cut off), against a 100 fold volume of CIB (with two changes). Two alternatives for separating chromosomes from cellular debris can be employed.

In the first approach, chromosomes are captured with magnetic beads conjugated to antibodies specific for the double stranded DNA of human chromosomes. These antibodies are present in sera of patients suffering from scleroderma (Chemicon International, Temecula, Calif.). The immunoglobulin fraction of the sera is isolated using protein A-agarose (Pierce, Rockford, Ill.). The IgG fraction is then biotinylated with biotin-NHS ester (Molecular Probes, Eugene, Oreg.) using the manufacturer's procedure. Streptavidin magnetic microbeads (Miltenyi Biotec, Auburn, Calif.) are used to bind the biotinylated IgG fraction of the human sera from scleroderma patients. The microbeads are then used to capture chromosomes. Chromosomes covered with magnetic beads are separated from non-chromosomal material by means of a strong field MACS Separator (Miltenyi Biotec). This approach also allows enrichment of occupied GMDs from the pool of mostly unoccupied GMDs.

In the second approach, cellular debris is separated from chromosomes using antibodies specific for cytoskeletal proteins conjugated to a solid support. In the chromosome release step, buffer containing detergent (Triton X-100) is used to solubilize membranes. But cytoskeletal proteins, such as fibronectin filaments, actin filaments, or intermediate microfilaments, are mostly present in an insoluble form. Although most microtubule proteins are solubilized by colcemid treatment, some remain. Antibodies against cytoskeletal proteins (fibronectin, actin, vimentin), are available from Accurate Chemical & Scientific (Westbury, N.Y.), Biosource International (Camarillo, Calif.) and Cytoskeleton (Denver, Colo.). These antibodies are conjugated through reductive amination to AminoLink Plus Coupling agarose gel (Pierce, Rockford, Ill.). 0.5 ml of antibody-derivatized gel (in a Compact Reaction Column, United States Biochemical, Cleveland, Ohio) is used to capture insoluble fragments of cellular debris by passing dialyzed and concentrated chromosome solution through a column.

Example 8

Detection with Chemiluminescent Substrates

Exothermic chemical reactions generally release energy in the form of vibrational or rotational excitation or heat. In chemiluminescent reactions, however, the electronically excited state is reached by a chemical reaction and light rather than heat is generated. The energy-rich source in most chemiluminescent reactions is peroxide, hydroperoxide, 1,2 dioxetane, or dioxetane bonds. During the transition of these excited intermediates to the electronic ground state, light is emitted in a process known as direct chemiluminescence. Novel acridane or dioxetane chemiluminescent substrates, developed by Tropix, BioTecx, and collaborators at Lumigen allow detection of $10^{-19}$ moles of horseradish peroxidase or $10^{-21}$ moles of alkaline phosphatase (74–76), a substantial improvement in sensitivity over fluorescence based detection at $10^{-14}$ moles per liter.

Chemiluminescent substrates for alkaline phosphatase are currently all phenyl phosphate dioxetanes (PPD). PPD (4-methoxy-4-(3-phosphatephenyl)spiro[1,2dioxetane,-3,2'-adamantane] disodium salt) or CSPD® (chlorine derivative of PPD) are now widely used in clinical immunossays and protein and nucleic acid detection test kits. PPD or CSPD® based substrates also contain fluorescent enhancers which promote more efficient generation of chemiluminescent light through extended glow kinetics.

Other substrates such as PS-1, a substrate for HRP which has just become commercially available, exploits Lumigen's discovery that esters of N-alkylacridancarboxylic acid are efficiently oxidized by peroxidase enzymes in the presence of hydrogen peroxide and a phenolic enhancer. The reaction, which requires only a minimal catalytic quantity of a peroxidase, converts the acridan compounds to the corresponding N-alkylacridinium ester. The PS-1 HRP substrate reaction produces an intense chemiluminescence, reaching a peak in approximately 10 minutes, with an extended decay over several hours. In a direct comparison with enhanced luminol based chemiluminescent reagents, previously the most sensitive system for detecting HRP, PS-1 was shown to be 100 times brighter (74).

The current detection limit using fluorescence in situ hybridization (FISH) and non-isotopically-labeled probes is approximately 100 kb DNA target or 10–30 copies of mRNA (77–79). Although slightly stronger signals can be obtained using probes labeled with radioactive isotopes, unacceptably long exposure times of days to weeks are required to detect approximately the same length DNA targets. Furthermore, health and disposal concerns make this technology unsuitable for most laboratories.

In situ hybridization techniques have dramatically improved in recent years both in terms of safety and sensitivity, primarily due to use of enzymes instead of isotopes as reporter molecules. Due to high reaction turnover, horseradish peroxidase (HRP) or alkaline phosphatase (AP) are the most frequently used reporter enzymes. Using reporter enzymes, localization of hybridization signals can be performed either with calorimetric immunohistochemistry methods, which are less sensitive, or with fluorescent methods, which increase sensitivity 10–100 fold, in comparison to the non-enzymatic methods (80).

The highest detection limits for both reporter enzymes are obtained, however, using chemiluminescent substrates which facilitate the emmission of light triggered by an enzymatic reaction. Approximate detection limits of several approaches are shown below.

| Detection Method | Detection Limit[a] | Base Pairs[b] |
|---|---|---|
| Color | $10^{-10}$–$10^{-12}$ | 200–400 |
| Fluorescence | $10^{-13}$–$10^{-15}$ | 100–200 |
| Radioisotopes | $10^{-20}$ | 10–100 |
| PCR | $10^{-22}$ | 0.4–10 |
| Chemiluminescence | $10^{-19}$–$10^{-21}$ | 10–100 |
| Microdrop CL-moles, kilobases, per each GMD | $10^{-21}$ | 10–100[c] |

Tyramide Signal Amplification

The recently available Tyramide Signal Amplification (TSA) system (NEN Life Sciences Products, Boston, Mass.) designed for fluorescence in situ hybridization was used in order to compare amplified fluorescence signal with chemiluminescence. TSA technology (80) uses horseradish peroxidase (HRP) to catalyze deposition of fluorophore or biotin labeled tyramide near the site of the hybridized probe, proximal to the enzyme. HRP can deposit $10^2$–$10^3$ tyramide molecules in 10 min, resulting in powerful signal amplification. In addition, since tyramide can be labeled both with fluorophores (TSA-Direct) and biotin (TSA-Indirect), both fluorescent or chemiluminescent signal can be detected.

For fluorescent measurements after MISH, GMDs were incubated in TNB blocking buffer (0.1M Tris-HCl, pH 7.5, 0.15M NaCl, 0.5% Blocking Reagent, NEN) with diluted conjugates of HRP with streptavidin for biotin labeled probes, or anti-fluorescein for fluorescein labeled probes (both from NEN) for 30 min. After three subsequent washes with TNT (0.1M Tris-HCl, pH 7.5, 0.15M NaCl, 0.05% TWEEN 20), GMDs were incubated with 300 µl of diluted fluorescein-tyramide for 10 min. Unreacted tyramide was removed by washing GMDs twice with TNT. MISH signals were then visualized using fluorescence microscopy.

Chemiluminescent Detection of Hybridized Probes

GMDs hybridized with biotin labeled probes were incubated for 30 min in TNB blocking buffer containing conjugate of either streptavidin-HRP (NEN) or HRP (Sigma) at dilutions of 1:100. GMDs hybridized with fluorescein-labeled probes were incubated with the conjugate of anti-fluorescein-HRP (NEN) diluted 1:100. In some signal amplification experiments, prior to chemiluminescent measurements, tyramide labeled with biotin was subsequently bound to streptavidin conjugate of either HRP or AP. Unreacted conjugates were removed by three successive washes with TNT. GMDs were than pelleted by low speed centrifugation and resuspended in 0.05 ml 0.4×SSC. Aliquots diluted in a ratio of 1:5 with the appropriate chemiluminescent substrate were than examined either using a microscope equipped with a photon counting device or a luminometer.

For horseradish peroxidase detection, three Luminol-based and one acridinium-based substrates were used. Two luminol-based substrates, LumiGLO™ and BM Chemiluminescence ELISA Substrate, were obtained from Kirkegaard and Perry Laboratories (KPL Inc., Gaithersburg, Md.) and Boehringer Mannheim Corp. (Indianapolis, Ind.), respectively. A third luminol-based substrate, NF-1, which does not require phenolic enhancers, was recently developed by BioTecx, Inc. (Houston, Tex.) and available for experimentation. The acridinium-based substrate, PS-1, was obtained from Lumigen, Inc. (Southfield, Mich.).

For alkaline phosphatase detection, two adamantyl 1,2-dioxetane aryl phosphate (PPD)-based substrates were used. Lumi-Phos 530, obtained from Lumigen, is a premixed formulation containing phenyl phosphate dioxetane, MgCl$_2$, cetyltrimethylammonium bromide, and an enhancer. CSPD, a derivative of PPD mixed with the Emerald II enhancer, was obtained from Tropix, Inc. (Bedford, Mass.).

GMDs were incubated in substrate solutions for 5–10 min at room temperature for HRP or 10–15 min at 37° C. for AP. Light emitted from GMDs soaked in chemiluminescent substrates was measured using an OPTOCOMP® I luminometer (MGM Instruments, Hamden, Conn.).

Derivatization of GMDs with HRP and AP

GMDs were formed from biotinylated agarose (FMC Bioproducts, Rockland, Me.) using standard emulsification procedures and sieved sequentially through 62 and 45 µm nylon mesh (Small Parts, Miami Lakes, Fla.) to obtain uniform size microdrops. GMDs were then blocked with TNB blocking buffer for 15 min. Aliquots containing 5×10$^5$ GMDs were reacted with appropriate dilutions of streptavidin-HRP or streptavidin-AP (both from Sigma) for 30 min. After binding, GMDs were washed 3 times with TNT washing buffer.

Digital Image Microscopy

For imaging chemiluminescence, an Olympus BH-2 microscope, equipped with phase contrast objectives for visualizing GMDs, was connected to a photon counting device through a C-mount. A Hamamatsu (Bridgewater, N.J.) C2400-32 ICCD (intensified CCD) camera was used as a photon counting device. The camera consists of an image intensifier and a CCD camera coupled with a relay lens and a control unit (Hamamatsu II controller, model M4314). In this configuration, the CCD camera effectively visualizes 756×485 pixels (pixel size 8.4×9.8 µm). Images were created and modified using the Hamamatsu ARGUS 20 Image Processor, which permits real time image observation.

For fluorescence imaging, the microscope was connected to a Hamamatsu C5985 cooled CCD camera and images were created using a Hamamatsu controller and an Argus 20 Image Processor. The CCD camera was cooled to 20° C. below the ambient temperature with a built in Peltier effect device. Both chemiluminescent and fluorescent images were analyzed and superimposed or pseudocolored using Adobe® Photoshop® 4.0 software (Adobe Systems, San Jose, Calif.) running on Windows® 95 operating system.

Results

This research has demonstrated the feasibility of detecting at least 2–10 kb DNA sequences located on single copy genes using probes hybridized to encapsulated nuclei and then imaged using microscopy and a CCD camera. A 2.2 kb DNA sequence of a single copy gene located on human chromosome Y can be detected using a chemiluminescent substrate for HRP. This sequence was not detectable using fluorescently labeled probes.

We evaluated a variety of substrates for both HRP and AP reporter enzymes. Although the lowest detection limit for HRP, measured in a luminometer, was obtained using acridinium-based substrate, low light level required for microscopic visualization destroyed the substrate. Two PPD (phenyl phosphate dioxetane) based substrates for AP were also unaffected by red light required to focus specimens for microscopy.

To detect low chemiluminescent light levels we used several CCD cameras, including a Hamamatsu Peltier effect-cooled CCD and a Photometrics CH250 cooled to −40° C. Low light levels generated from probe hybridizing to single copy gene sequences, which had approximately $4 \times 10^{2-10^3}$ molecules of reporter enzyme, were best detected using photon counting devices. By comparison, about $10^5$ reporter molecules of enzyme bound to agarose GMDs were needed for detection using a cooled CCD camera, such as the Photometrics CH250 (see Table 1 below).

TABLE 1

CCD camera detection limits for reporter enzyme molecules conjugated to streptavidin.

| CCD Camera | Reporter enzyme molecules detected/GMD |
| --- | --- |
| Hamamatsu C5985 CCCD | >$10^5$ |
| Photometrics CH250 CCCD | $10^5$ |
| Hamamatsu C2400-32 ICCD | $10^3$ |

Example 9

RNA Detection in Encapsulated Cells

The ability rapidly to detect the presence of virus-specific or cancer-specific RNAs in individual cells present in low frequences has applications in disease diagnosis, monitoring and treatment as well as blood screening. Microdrop in situ hybridization (MISII) is particularly suited for these applications because it eliminates the need for cell fixation and prevents cell clumping which makes the detection of rare cells diffcult. This examples describes detecting both cancer cells (positive for telomerase mRNA expression) and HIV-infected cells by using a combination of MISH and flow cytometry.

Materials and Methods

1. Cell Lines and Culture Conditions

Human promyelocytic leukemia HL-60 cells leukemia were purchased from American Type Culture Collection (ATCC, Rockville, Md.). A3.01 cells and HIV infected cells H9/HTLV-III NIH 1983 were obtained from the NIH AIDS Research and Reference Reagent Program, Rockville, Md. All cells were cultured in RPMI 1640 medium supplemented with 10% fetal bovine serum (FBS) and were grown at 37° C. in the presence of 5% $CO_2$.

2. Probes and Fluorescent Labeling

Oligonucleotide probes for detecting RNA labeled with fluorescein at 5' end were purchased from Oligoes Etc., Wilsonville, Oreg. Oligos labeled with horseradish peroxidase were purchased from Biosorce International, Camarillo, Calif. Oligonucleotide probes for detection of HIV RNA are derived from gag region of HIV genome. Sequences of oligonucleotide probes are depicted below:

HIV RNA detection

H1 5'-(HRP)CCA TTC TGC AGC TTC CTC ATT GAT GGT CTC-3'

H2 5'-(HRP)CTT GTC TTA TGT CCA GAA TGC TGG TAG GGC-3'

Telomerase mRNA Detection

BF-1 5'FITC-CCA ACA AGA AAT CAT CCA CCA AAC GCA GGA GC 3'

BF-3 5'FITC-GAG GCT GTT CAC CTG CAA ATC CAG AAA CAG 3'

BF-4 5'FITC-GAA GGT TTT CGC GTG GGT GAG GTG AGG TG 3'

3. Cell Encapsulation

Human cells harvested from various stages of growth were pelleted by low speed centrifugation, washed with Hanks Balanced Salt Solution (HBSS) containing 0.1% diethylpyrocarbonate (DEPC), and resuspended in the same buffer at concentrations $20 \times 10^6$ cells per ml. For encapsulation of cells, pluronic acid was used as a surfactant because it does not affect cell membrane integrity during emulsification.

A cell-agarose mixture (2.3% Type XII agarose and 0.1% pluronic acid in IIBSS containing $2 \times 10^6$ cells per 0.52 ml) was prepared by melting 0.4 ml agarose in HBSS at 100° C., cooling the agarose to 57° C., and adding 100 µl of cell suspension and 20 µl of 10% pluronic acid. The mixture was held at 65° C. for 5 min and then quickly added dropwise to 15 ml of CelMix™ 200 emulsion matrix (One Cell Systems, Cambridge, Mass.) pre-warmed to 6° C. Gel microdrops were created using a CellSys100™ Microdrop Maker (One Cell Systems, Cambridge, Mass.) equipped with a 1.6 cm blade using successive rotor speeds of 2,200 rpm for 1 min at 20–25° C., 2,200 rpm for 1 min at 0° C., and 1,200 rpm for 7 min at 0° C. The GMDs were then separated from the emulsion matrix by centrifugation at 400×g for 7 min. The pellet containing encapsulated cells was washed twice with DEPC treated HBSS and stored at 4° C. in the same buffer and used within a week. However, encapsulated cells can be stored long-term (at least for a month) in 70% ethanol at −20° C.

4. Microdrop In Situ Hybridization (MISH) of Encapsulated Human Cells

All solutions used for cellular RNA detection were prepared in DEPC treated water. 1 $\mu$l of DEPC (10% in 70% ethylalcohol) was added to approximately 100,000 GMDs containing 10,000 cell-occupied GMDs in a volume of 50 $\mu$l. After a 15 min incubation at room temperature, an equal volume of 2×hybridization buffer was added and the mixture was incubated for a given time at temperatures ranging from 50 to 58° C. For hybridization with the oligo probes, 2×hybridization solution contained, 1.2 M Tris-IIC1, pH 8.0, 0.1 mg/ml salmon sperm DNA, 0.1 mg/ml *E. coli* tRNA, 100 units of placental RNAsc inhibitor/ml and 200 $\mu$l of Vanadyl Ribonucleoside Complex/ml (BRL, Bethesda, Md.). Before mixing with encapsulated cells 10–20 picomoles/0.1 ml of oligonucleotide probes were added to 2×hybridization buffer. After performing hybridization at 55° C., GMDs were washed using wash buffer (WB, 0.05 M Tris-IIC1, pH 0.0, 0.15 M NaCl, 0.2 mM EDTA, 0.1% Tween 20) at temperatures ranging from 20 to 55° C. Hybridization signals were amplified by a Tyramide Signal Amplification (TSA, NEN™ Life Science Products, Boston, Mass.) either directly (with HRP labeled probes) or after binding with anti-fluoresecin-HRP (with fluorescein-labeled probes).

To detect HIV RNA with oligo probes directly labeled with HRP, encapsulated cells were first washed three times with HRP stabilizing buffer (Biotecx, Cambridge, Mass.) before adding 2×hybridization buffer.

5. Tyramide Signal Amplification

The Tyramide Signal Amplification (TSA) system (NEN Life Sciences Products, Boston, Mass.) is designed for non-isotopic in situ hybridization. TSA technology (37) uses horseradish peroxidase (HRP) to catalyze deposition of tyramide labeled with fluorophores near the site of the hybridized probe, proximal to the enzyme. HRP can deposit $10^2$–$10^3$ tyramide molecules in 10 min, resulting in powerful signal amplification. After MISH, GMDs were incubated in TNB blocking buffer (0.1M Tris-HCl, pH 7.5, 0.15 M NaCl, 0.5% Blocking Reagent, NEN) with 1:200 diluted conjugate of anti-fluorescein HRP (NEN) for 30 min. After three subsequent washes with TNT (0.1 M Tris-HCl, pH 7.5, 0.15 M NaCl, 0.05% Tween 20), GMDs were incubated with 1:100 diluted tyramide-fluorescein for 10 min. Unreacted tyramide was removed by washing GMDs twice with TNT.

6. Microscopy and Digital Image Analysis

The integrity of encapsulated cellular nucleic acids (both DNA and RNa after fluorescent staining with 0.2 $\mu$g/ml acridine orange) and MISH fluorescence signals were examined visually using an Olympus BH-2 microscope (phase contrast 40×SPlan 0.4 objective) equipped for epifluorescence with appropriate filters for DAPI, fluorescein or phycoerythrin. Digital images were taken with a cooled CCD camera (B/W Hamamatsu C5985-02 with control unit) connected to the microscope. Digital images were processed with the assistance of computer software (Adobe Photoshop version 4.0, Adobe Systems, San Jose, Calif.).

7. Flow Cytometric Analysis of Encapsulated Cells after MISH

Flow cytometric analysis after MISH was performed using an EPICS Elite™ (Coulter Corporation, Miami, Fla.). 15 mW of a 488 nm line of an air cooled argon laser was used to excite the fluorescein in hybridized probes. The trigger parameter for collecting events was forward scatter (detecting encapsulated cells). 10,000 list mode events were collected at a rate of approximately 600 occupied GMDs per second and analyzed using elite 4.01 software.

Results

Figure 7:
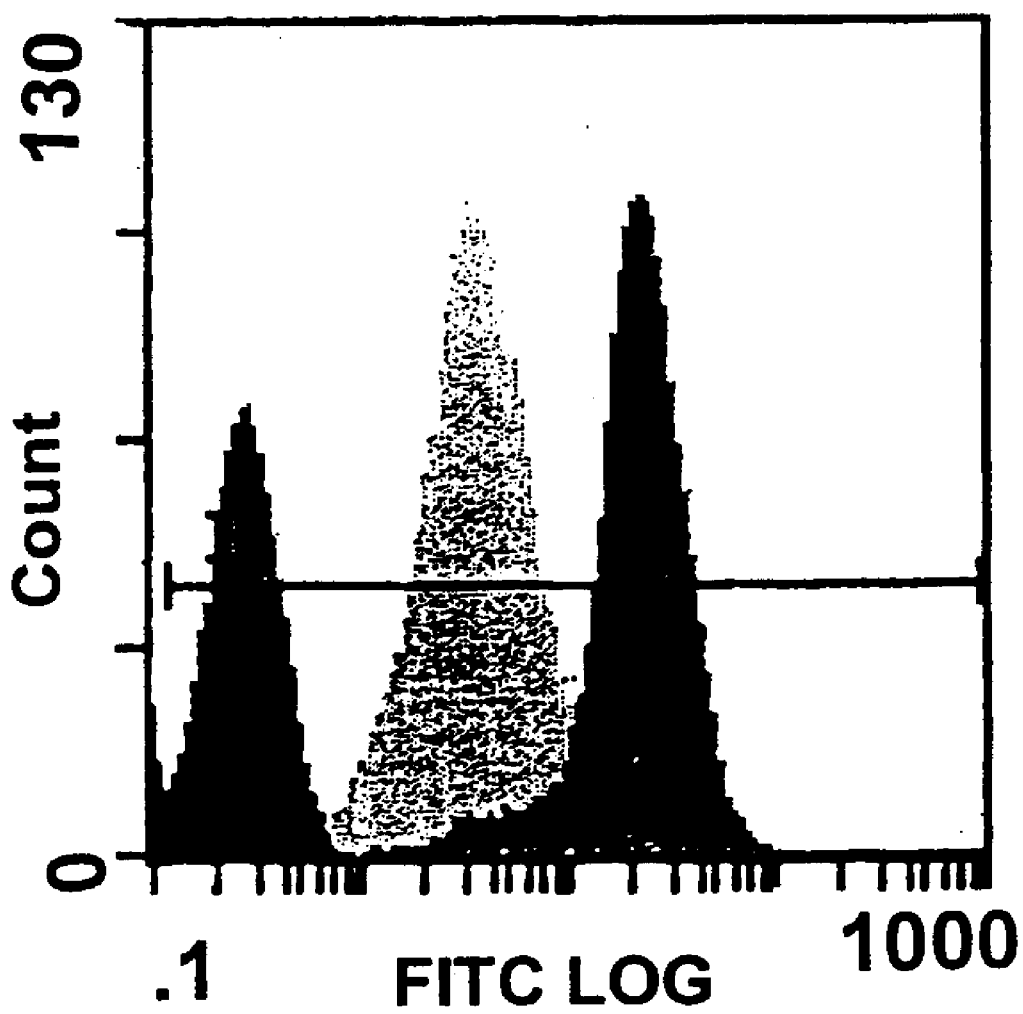
FIG. 7 shows flow cytometric detection of gag HIV RNA in encapsulated HIV infected cells after hybridization with two HRP-labeled oligo probes.

FIG. 7 shows flow cytometric detection of gag HIV RNA in encapsulated HIV infected cells after hybridization with two HRP-labeled oligo probes. A2.01 cells with the same lineage as H9 cells were used as control cells. Both control and HIV infected cells were vultured for 4 days. The peaks are color coded and represent the following: Red peak, A3.01 cells, probes not present (mean fluorescence 0.258); Blue peak, H9 HTLVIII cells, probes not present (mean fluorescence=0.289); Yellow peak, A3.01 cells, probes present (mean fluoresce ce=3.41); Green peak, H9HTI.VIII cells, probes present (mean fluorescence-19.2). Mean fluorescence of HIV infected and non-infected cells hybridized with oligo probes was used for the calculation of S/N value, which was found to be 5. It has previously been estimated that H9/HTLV-III cells express approximately 250–500 copies of HIV-specific RNA. Detection of such a low copy RNA number indicates the sensitivity of the assay for detection of HIV-infected cells in human blood.

Figure 8:
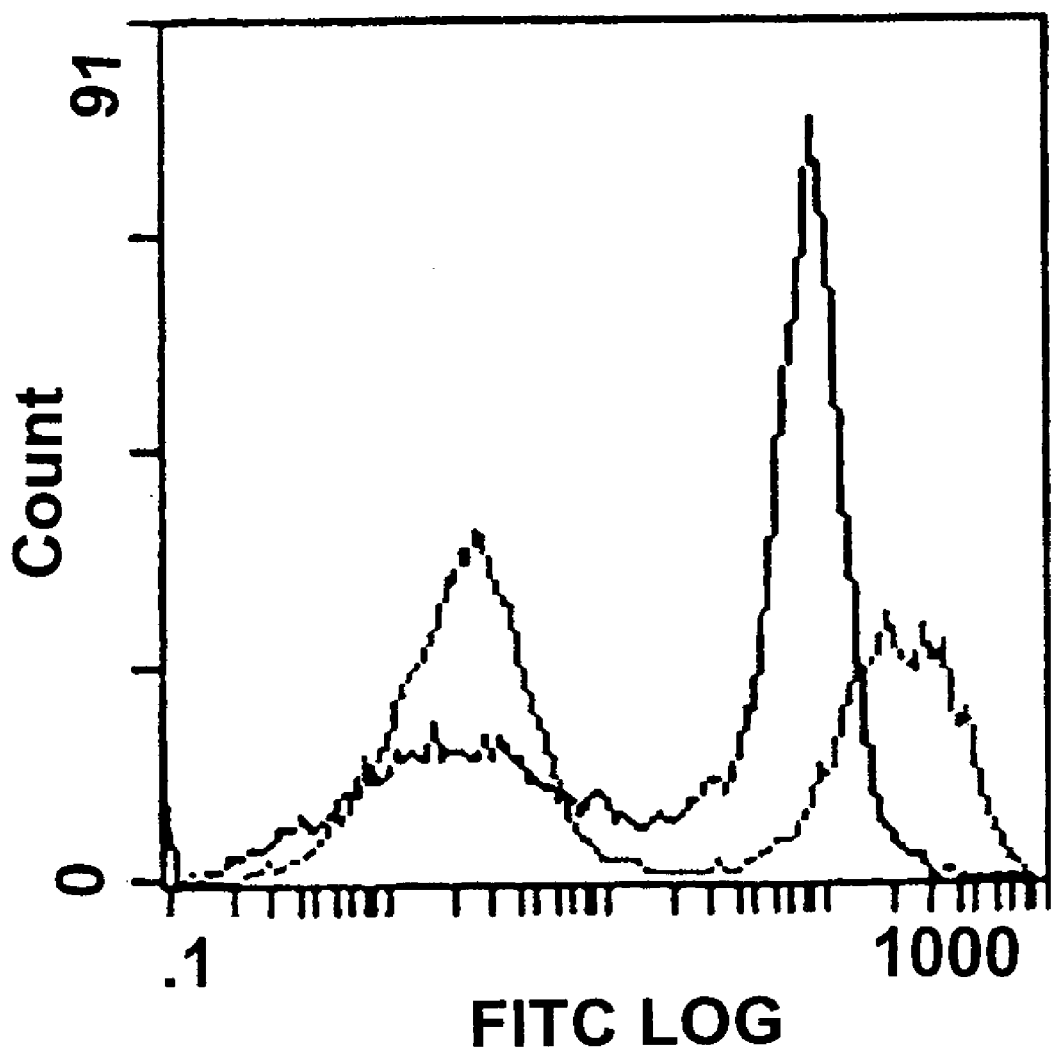
FIG. 8 shows detection of telomerase mRNA in HL-60 (model cancer cell line) and human PBMCs using fluorescein-labeled oligonucleotide probes.

FIG. 8 shows detection of telomerase mRNA in HL-60 (model cancer cell line) and human PBMCs using fluorescein-labeled oligonucleotide probes followed by TSA signal amplification. Hybridization conditions and TSA amplification are described in Materials and Methods. The histograms are color coded as follows: red=HL-60 cells; black=human PBMCs. Left peak represents unoccupiewd GMDs and right peak represents GMDs occupied with single cells. The relative mean fluoresence of the right peaks in 220 for HL-60 cells and 78 for human PBMCs (S/N-2.8). These results show the power of this methodology for detecting differential expression of mRNA in different cell types, and particularly between normal and cancer cells.

BIBLIOGRAPHY

1) Powell, Ph.D. Thesis, Massachusetts Institute of Technology, 1989.
2) Powell & Weaver, Bio/Technology 8:333–37, 1990.
3) Weaver, Methods, Academic Press, Vol. 2, No.3:234–247, 1991.
4) Weaver, Bio/Technology 9:873–876, 1991.
5) Weaver, Bio/Technology 6:1084–89, 1988.
6) Williams, J. Clin Micro 28:1002–8, 1990.
7) Abebe, Am. J. Hum. Genetics 53:1264, 1993.
8) Abebe, In Situ hybridization to HIV-1 RNA in gel microdrops, American Society for Cell Biology, 1993.
9) Nguyen, Cytometry, 21, 111–119, 1995.
10) Trnovsky, Am. J. Hum. Genetics, 59:p A135, 1996.
11) Trnovsky, Poster 46 In The San Diego Conference on Nucleic Acids presented as section of American Association for Clinical Chemistry, November 1996.
12) Collins, Science, 262:43–46, 1993.
13) Bartholdi, Methods in Enzymology Vol.151, 252–267, 1987.
14) Gray, in Flow Cytogenetics, J W Gray (ed), Academic Press, pp. 137–149, 1989.
15) Young, in Flow Cytogenetics, J W Gray (ed), Academic Press, pp. 1–13, 1989.
16) Latt, in Flow Cytogenetics, ed. Grey J W, Acadenic Press, pp.243–256, 1989
17) Shizua, P.N.A.S,USA 89:8794–8797, 1992.
18) Current Protocols in Human Genetics John Wiley & Sons, ed. by Dracopoli N C, et al.,1996.
19) Smith, Methods in Enzymology , Academic Press, Vol.155, p.449, 1987.
20) Carter, J. Med. Genetics, 29:299–307, 1993.
21) Dolezel, in Kew Chromosome Conference IV, ed. Brandham E, and Bennett M D.,p.185–200, Royal Botanic Garden,Kew, 1995.
22) Macas, Biotechniques, 402–408, 1993.
23) Matsukuawa, Cancer Research, 53:1328–1331, 1993.

24) Boyle, Genomics 12:517–525, 1992.
25) Vooijs, Am. J. Hum. Genet.,52:586–597, 1993.
26) Weier, Generation of five high complexity painting probe libraries from flow-sorted mouse chromosomes, Genomics (submitted).
27) Bauman "Flow Cytometric Measurement of Specific DNA and RNA Sequences," in: *Flow Cytogenetics*, J W Gray (ed), Academic Press, pp. 276–303, 1989.
28) Shapiro, Practical Flow Cytometry, third edition, Wiley-Liss, p.284, 1995.
29) Cram, Chromosome analysis and sorting. In 1996 Annual course in flow cytometry; applications in immunobiology and cell biology, Brunswick, Me., p20, 1996.
30) Human Chromosomes: Principles and Techniques, ed.Verma RS and Babu A.,McGraw-Hill, 1995.
31) Abebe, (1993), Amer. J. Hum. Genetics. 53:1264.
32) Abebe, (1993) In Situ Hybridization to HIV-1 RNA in Gel Microdrops, American Society for Cell Biology.
33) Nguyen, (1995), Cytometry 21:111–119.
34) Cline, (1994) New Engl. J. Medicine 330:328–336.
35) Vogelstein B. (1990), Nature 348:681–682.
36) Yamamoto T, (1993), Microbiology and Immunology 37:11–22.
37) Daley (1990), Science 247:824–26.
38) Rowley (1990), Cancer Res. 50:3816–25.
39) Smith (1993), Clinical Genetics 43(1):5–8.
40) Tkachuk, (1990), Science 250(4980):559–62.
41) Devilee, Cancer Res 5825–5830.
42) Escudier, Blood 81: 2702–2707.
43) Kallioniemi (1992), PNAS 89:5321–5.
44) Farrell S A. (1991), Am J Med Genetics 40:345–7.
45) Weier, (1993) PCR, DNA Sequence 4:47–51.
46) Scherthan, (1994) Nature Genetics.
47) Bellanne-Chantelot, Cell 70:159–168.
48) Goguen B and Kedersha N (1993), Nature 363:189–90.
49) Telenius, (1992), Genes, Chromosomes and Cancer 4:257–263.
50) Weier, Genomics (submitted).
51) Crisan, (1993) The bcr/abl rearrangements in chronic myelogenous leukemia and acute leukemias: Clinical perspectives and quality controls, In Farkas D H, (ed.) Molecular Biology and Pathology: A Guidbook for Quality Control. San Diego, Academic Press pp. 103–121.
52) Kawasaki al. (1988), PNAS 85:5698–5702
53) Inokuchi (1991), Blood 78:3125–3127.
54) Naumowski (1988), Cancer Research 48: 2876–2879.
55) Crisan (1994), Diagnostic Hematology 8:725–750.
56) Weaver (1988), Bio/Technology 6:1084–1089.
57) Weaver (1991), Methods, Academic Press, Vol. 2, p. 234–247.
58) Weaver (1991), Bio/Technology 9:873–876.
59) Powell (1990), Bio/Technology 8:333–7.
60) Gray (1995), J. Imm. Meth. 182:155.
61) Weaver, Antibody secretion assay using gel microdrops and flow cytometry, in Flow Cytometry Applications in Animal Cell Culture. Ed. Al-Rubeai and Emery. Marcel Dekker, New York, N.Y., 39–62, 1995.
62) Ryan, (1995) *J. Clin. Microbiol.* 33:1720–1726.
63) Blumenthal (1979), J. Cell. Biol. 81:255–259
64) Sillar (1981), J. Histochem. Cytochem. 29P: 74–78
65) Cram (1983), Cancer Res. 43:4828–4837
66) Chen (1994), WO 94/02641.
67) Weaver (1991) In Methods, Academic Press, 2(3):234.
68) Abebe (1993) Mol.Biol.Cell, 4:113A.
69) Nguyen (1995) Cytometry, 21:111.
70) Trnovsky et al.(1996) Am. J. Hum. Genetics, 59:pA135
71) Powell (1990), Bio/Technology, 8:33.
72) Ryan, (1995), J Clin Micro., 33:1720.
73) Kenny, (1995), Bio/Technology, 13:787.
74) Akhavan-Tafti (1994), New chemiluminescent substrates for the detection of horseradish peroxidase, In Bioluminescence and Chemiluminescence ed. A. K. Campbell, L. J. Kricka and P. E. Stanley) John Wiley and Sons p. 198.
75) Schaap (1989) Clin.Chem. 35(9):1863.
76) Bronstein (1994) Analytical Biochemistry 219:169.
77) Herrington (1990) Non-isotopic in situ hybridization in human pathology, in In Situ Hybridization: Application to Developmental Biology and Medicine, ed. Harris N, and D G Wilkinson, Cambridge University Press, p. 241.
78) Raap (1992), In situ hybridization for molecular cytogenetics, in In Situ Hybridization: Medical Applications, ed. Coulton G R, and J de Belleroche, Kluwer Academic Publishers, p.97
79) Nuovo, (1992) In Situ Hybridization: Protocols and Applications, Raven Press, New York.
80) Litt, (1996) A high sensitivity signal enhancement method. American Biotechnology Laboratory, December, p.16.
81) Shaw (1995), Biotechniques, 19:945.
82) Rushbrooke (1993), Luminescence imaging in the life sciences using an intensified CCD system, in Bioluminescence and Chemiluminescence. Ed. Szalay A A, L J Kricka and P E Stanley. Proceedings of the 7th International Symposium on Bioluminescence and Chemiluminescence held in Banff, Canada, John Wiley &Sons p.28.
83) Carter, (1993) Science, 259:1330.
84) Vergnaud, (1986), Am.J.Hum.Genet., 38:109

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A method of nucleic acid analysis, comprising
forming a population of gel microdrops encapsulating a population of biological entities, each entity comprising a nucleic acid, whereby at least some microdrops in the population each encapsulate a single entity;
crosslinking hydroxyl groups in the agarose of the microdrops with each other and with hydroxyl groups in the nucleic acids encapsulated in the microdrops;
contacting the population of gel microdrops with a probe under conditions whereby the probe specifically hybridizes to at least one complementary sequence in the nucleic acid in at least one gel microdrop;
analyzing the nucleic acid encapsulated with the microdrop by isolating or detecting the at least one gel microdrop;
wherein the cross-linking is reversible without damage to the nucleic acids encapsulated in the microdrops.

2. A method of nucleic acid analysis, comprising
forming a population of gel microdrops encapsulating a population of biological entities, each entity comprising a nucleic acid, whereby at least some microdrops in the population each encapsulate a single entity;
crosslinking hydroxyl groups in the agarose of the microdrops with each other and with hydroxyl groups in the nucleic acids encapsulated in the microdrops;

contacting the population of gel microdrops with a probe under conditions whereby the probe specifically hybridizes to at least one complementary sequence in the nucleic acid in at least one gel microdrop;

analyzing the nucleic acid encapsulated with the microdrop by isolating or detecting the at least one gel microdrop; and releasing the nucleic acids from the microdrops after the contacting step.

3. A method of nucleic acid analysis, comprising forming a population of gel microdrops encapsulating a population of biological entities, each entity comprising a nucleic acid, whereby at least some microdrops in the population each encapsulate a single entity;

crosslinking hydroxyl groups in the agarose of the microdrops with each other and with hydroxyl groups in the nucleic acids encapsulated in the microdrops;

contacting the population of gel microdrops with a probe under conditions whereby the probe specifically hybridizes to at least one complementary sequence in the nucleic acid in at least one gel microdrop;

analyzing the nucleic acid encapsulated with the microdrop by isolating or detecting the at least one gel microdrop;

wherein the cross-linking is performed using divinyl sulfone.

4. The method of any one of claims 1–3, wherein the biological entities are selected from the group consisting of cells, viruses, nuclei and chromosomes.

5. The method of any one of claims 1–3, wherein the biological entities are not fixed chemically before the contacting step.

6. The method of any one of claims 1–3, wherein the biological entities are chromosomes.

7. The method of any one of claims 1–3, wherein the population of gel microdrops is formed by forming a preparation of biological entities in a liquid gel, and dispersing the preparation into a hydrophobic solvent to form drops encapsulating the entities.

8. A method of nucleic acid analysis, comprising forming a population of gel microdrops encapsulating a population of biological entities, each entity comprising a nucleic acid, whereby at least some microdrops in the population each encapsulate a single entity;

crosslinking hydroxyl groups in the agarose of the microdrops with each other and with hydroxyl groups in the nucleic acids encapsulated in the microdrops;

contacting the population of gel microdrops with a probe under conditions whereby the probe specifically hybridizes to at least one complementary sequence in the nucleic acid in at least one gel microdrop;

analyzing the nucleic acid encapsulated with the microdrop by isolating or detecting the at least one gel microdrop;

wherein the populations of gel microdrops is formed by forming a preparation of biological entities in a liquid gel and passing the preparation through a pulsating orifice of an ink jet printer.

9. The method of any one of claims 1–3, wherein most drops contain zero chromosomes, and 1–30% of drops contain a single chromosome.

10. The method of any one of claims 1–3, wherein the drops are 2–200 μm in diameter.

11. The method of any one of claims 1–3, wherein the gel is selected from agarose, alginate, carrageenan, or polyacrylamide.

12. The method of any one of claims 1–3, wherein the biological entities are obtained from a human, nonhuman mammal, plant, bacterium, fungus, fish, or insect.

13. The method of claim 6, wherein the population of chromosomes are obtained from a single cell or a homogeneous cell line from a patient.

14. The method of any one of claim 1–3, further comprising labelling microdrops containing an entity with a second label without labelling empty microdrops with the second label.

15. The method of claim 6, wherein the population of chromosomes is obtained from a population of different cells in a patient.

16. The method of any one of claims 1–3, further comprising storing a gel microdrop encapsulating a biological entity for at least one hour.

17. The method of claim 16, wherein the biological entity is stored before the contacting step.

18. A method of nucleic acid analysis, comprising forming a population of gel microdrops encapsulating a population of biological entities, each entity comprising a nucleic acid, whereby at least some microdrops in the population each encapsulate a single entity;

crosslinking hydroxyl groups in the agarose of the microdrops with each other and with hydroxyl groups in the nucleic acids encapsulated in the microdrops;

contacting the population of gel microdrops with a probe under conditions whereby the probe specifically hybridizes to at least one complementary sequence in the nucleic acid in at least one gel microdrop;

analyzing the nucleic acid encapsulated with the microdrop by isolating or detecting the at least one gel microdrop; and storing a gel microdrop encapsulating a biological entity for at least one hour after the isolating or detecting step.

19. The method of claim 16, wherein the gel microdrop is stored for at least six months.

20. A method of diagnosing a disease due to a mutation, comprising:

obtaining a sample of cells from a patient;

encapsulating a population of chromosomes from the sample in a population of microdrops;

crosslinking hydroxyl groups in microdrops with each other and with hydroxyl groups in the nucleic acid between the denaturation and contacting steps contacting the microdrops with a first probe that is complementary to a nucleic acid segment containing a somatic mutation, and a second probe complementary to the chromosome in which the somatic mutation occurs at a site distal to the somatic mutation, whereby the first probe hybridizes to microdrops bearing the chromosome with a somatic mutation and the second probe hybridizes to microdrops bearing the chromosome irrespective whether the somatic mutation is present;

determining a ratio of microdrops hybridizing to the first probe and hybridizing to the second probe;

diagnosing the existence or prognosis of the disease from the ratio.

21. The method of claim 20, wherein the disease is cancer.

22. The method of claim 20, wherein the mutation occurs in a p53, BRCA-1, BRCA-2, ras or retinoblastoma gene.

* * * * *